(12) United States Patent
Hickle

(10) Patent No.: US 7,150,735 B2
(45) Date of Patent: Dec. 19, 2006

(54) DRUG CONTAINER ENTRY MECHANISMS AND METHOD

(75) Inventor: Randall S. Hickle, Lubbock, TX (US)

(73) Assignee: Scott Laboratories, Inc., Lubbock, TX (US)

( * ) Notice: Subject to any disclaimer, the term of this patent is extended or adjusted under 35 U.S.C. 154(b) by 331 days.

(21) Appl. No.: 10/439,327

(22) Filed: May 16, 2003

(65) Prior Publication Data

US 2003/0229330 A1   Dec. 11, 2003

Related U.S. Application Data

(60) Provisional application No. 60/378,046, filed on May 16, 2002.

(51) Int. Cl.
*A31B 19/00* (2006.01)
*A61M 1/00* (2006.01)

(52) U.S. Cl. .................. 604/411; 604/272; 604/27; 604/403

(58) Field of Classification Search ............. 604/6.05, 604/27, 28, 30, 43, 44, 83, 85–88, 151–155, 604/164.02, 506, 508, 519–520, 181, 187, 604/188, 262, 272–74, 159, 403, 411, 412–416, 604/163, 171, 164.08, 194; 210/252, 256, 210/257.1, 258, 198.1, 282; 417/477.2, 437, 417/439, 472, 474
See application file for complete search history.

(56) References Cited

U.S. PATENT DOCUMENTS

| | | | | |
|---|---|---|---|---|
| 4,826,492 A | * | 5/1989 | Magasi ................ 604/274 |
| 5,324,258 A | * | 6/1994 | Rohrbough ............ 604/86 |
| 6,022,339 A | * | 2/2000 | Fowles et al. .......... 604/411 |
| 6,045,533 A | * | 4/2000 | Kriesel et al. .......... 604/132 |
| 6,063,052 A | | 5/2000 | Uber, III et al. | |
| 6,202,708 B1 | * | 3/2001 | Bynum .................. 141/9 |
| 6,582,415 B1 | | 6/2003 | Fowles et al. | |

OTHER PUBLICATIONS

"Needle-Free Dispensing Pins" Catalog page from www.bbraunusa.com illustrating composition of DP1000 Mini Spike. Printed Jan. 24, 2006.*

* cited by examiner

*Primary Examiner*—Tatyana Zalukaeva
*Assistant Examiner*—Leslie R. Deak
(74) *Attorney, Agent, or Firm*—Hogan & Hartson LLP

(57) ABSTRACT

The invention of this application relates generally to intravenous (IV) infusion of drugs to patients, and more particularly to aspects of an IV infusion system comprising an infusate cassette and an infusate container. The present invention provides a drug infusion cassette that incorporates a strong vial spike that may be non-metal, a means for sheathing the spike when it is not in use, an anti-free flow device, and other beneficial features such as an air entrainment lockout mechanism, quality assurance tags, stopcocks made of soft materials and means of securing tubing to the cassette with a minimum of individual parts. The drug cassette can be used with an automated spiking mechanism comprising a motorized vial holder that holds a vial. The spike remains sheathed if the drug cassette is not fully engaged with a mating surface of devices such as a pumping unit or a sedation and analgesia delivery system.

28 Claims, 16 Drawing Sheets

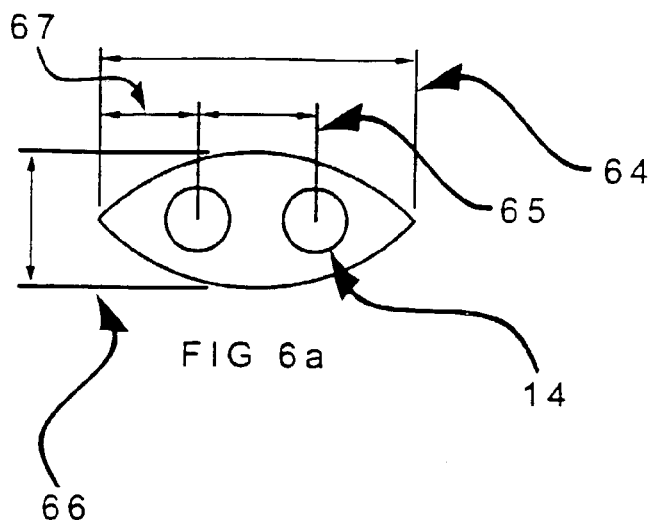
FIG 6a
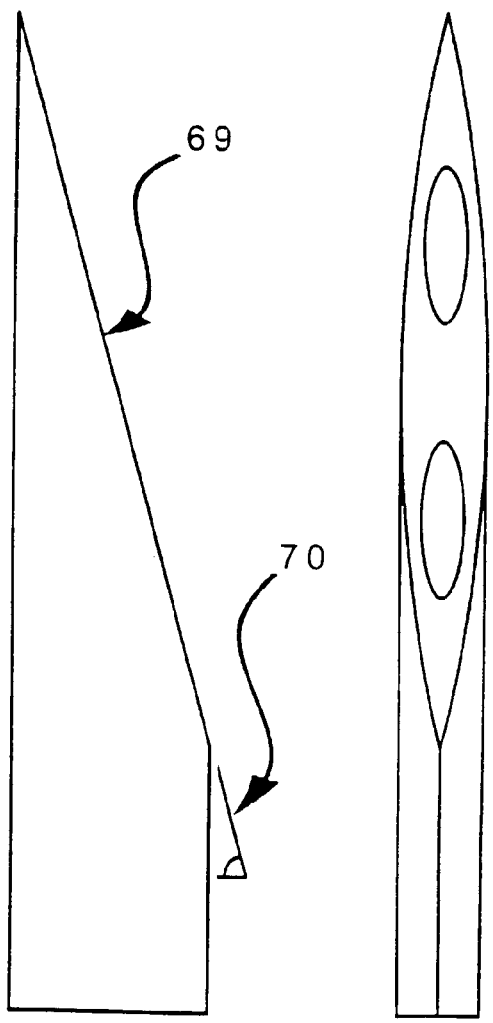
FIG. 6b
FIG. 6c
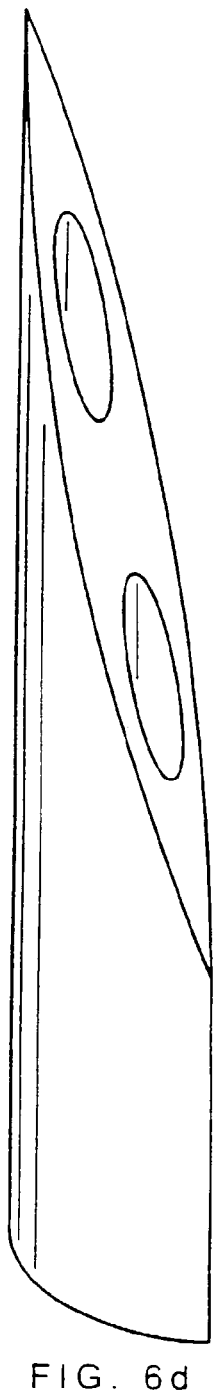
FIG. 6d
FIG. 6

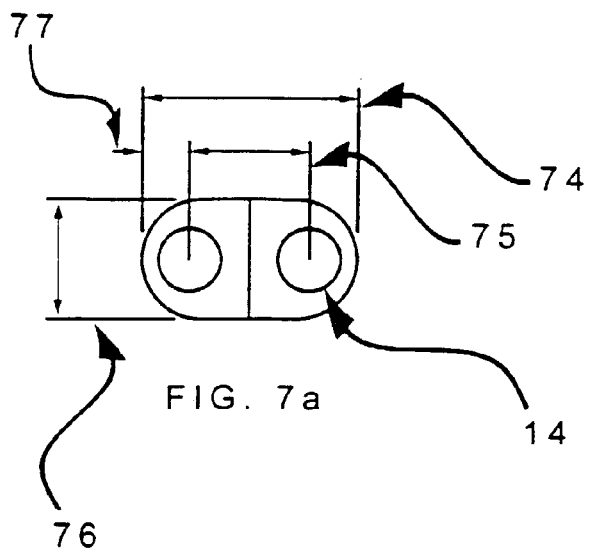
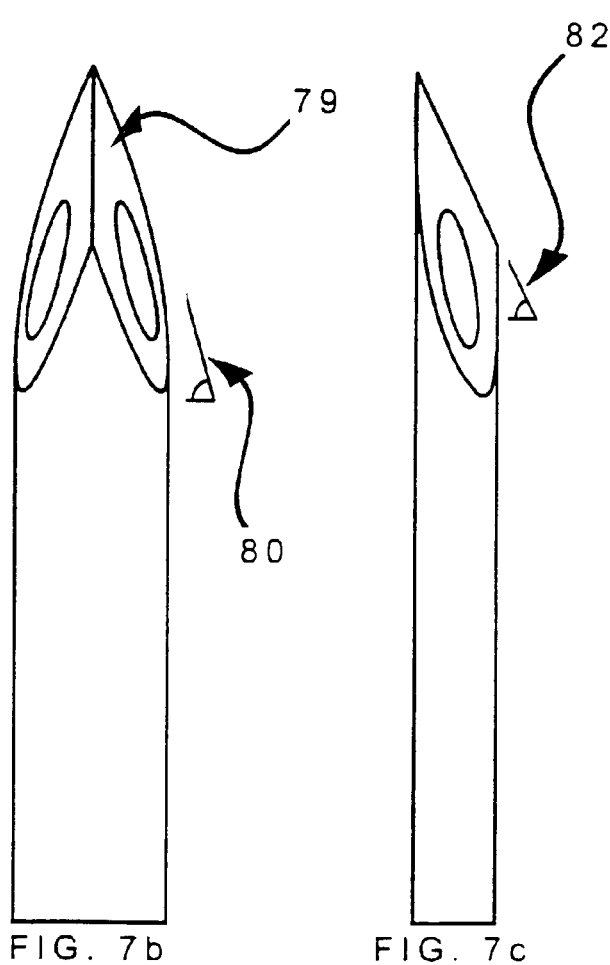
FIG. 7a
FIG. 7b
FIG. 7c
FIG. 7d
FIG. 7

DRUG CONTAINER ENTRY MECHANISMS AND METHOD

CROSS REFERENCE TO RELATED APPLICATIONS

This application claims priority under 35 U.S.C. §119(e) to U.S. Provisional Patent Application No. 60/378,046, "Drug Container Entry Mechanisms," filed May 16, 2002, which is hereby incorporated by reference.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Field of the Invention

The invention of this application relates generally to intravenous (IV) infusion of drugs to patients, and more particularly to aspects of an IV infusion system comprising an infusate cassette and an infusate container.

2. Description of Related Art

Mechanically controlled infusion of a liquid drug from a reservoir to a patient is a useful process of administering a drug. An electro-mechanically controlled infusion process often provides a much steadier and more accurate administration of a drug than is possible from a human giving injections. By letting a computer model determine flow rates of drug, an electro-mechanically controlled infusion device can be programmed such that the concentration of the drug at a patient's effect site compartment remains steadily within the drug's therapeutic range.

Various medical devices for controlling the infusion of a liquid directly to a patient are known. Certain of these devices utilize pumping mechanisms to deliver liquid drugs from a reservoir such as a syringe, a collapsible bag, or a vial to a patient supply tube. One example of such a device, shown in U.S. Pat. No. 6,186,977, includes a liquid drug supply in a collapsible bag and an infusion pump, which draws the drug directly from the supply and moves it along a flow passage to a patient supply tube.

Certain of these medical devices further utilize drug pump cassettes, which provide a rigid housing and pressure plate that interact with the pumping mechanisms of the devices. These cassettes serve as intermediary devices between drug containers and patient supply lines. A typical cassette includes a passage, which is acted upon by the pumping mechanism of an infusion device to move the drug along to the supply line.

One example of a cassette for use with a drug pumping system, shown in U.S. Pat. No. 6,165,154, has a fluid passage and a collapsible pressure conduction chamber for generating a pressure gradient to move drug along the passage. Certain other cassettes are known which provide means for moving drug along a flow channel. One example of this other type of cassette, shown in U.S. Pat. No. 6,202,708, provides a large chamber for mixing a powdered drug with a liquid solvent. The cassette also includes a pressure plate, which supports a fluid flow passage against which a peristaltic pump may act to move the liquid along to a patient delivery tube.

The above and other drug infusion cassettes generally have a sharp spike upon which a drug vial is impaled to provide access to the contents of the vial. Drug infusion cassettes that incorporate a sharp spike or trocar for penetrating a vial stopper may be considered as a sharp device, especially if the spike is exposed and able to cause an accidental sharps injury. The International Health Care Worker Safety Center has computed that 590,164 needlestick and sharps injuries occur annually in the United States. "Sharps" boxes are often employed to collect used sharp devices like needles and scalpels. A user drops a sharp device into a sharps box immediately after use to prevent accidental sharps injuries like needle sticks that may result in transmission of disease and blood-borne pathogens. Sharps boxes generally have a small opening that prevents a hand from being inserted into the sharps box, and may not accept larger devices such as drug infusion cassettes.

Because drug cassettes are generally disposable and intended for single use, low manufacturing cost is desirable if an end product is to be competitive. Reduction of parts count may decrease inventory, cost of materials and assembly time, leading to lower manufacturing costs.

In certain situations, a disposable drug cassette may be used on the same patient with more than one drug vial. In those situations where multiple vial spikings will occur, a spike on a drug cassette has to reliably withstand repeated forces and stresses imposed upon it by multiple spiking cycles.

An ever-present concern with drug cassettes and drug infusion systems is "free flow" whereby drug in a vial, or residual drug in intravenous tubing, flows via gravity into a patient in an uncontrolled manner, especially in the case of potent drugs. Free flow of drugs is also possible even if a drug vial is not spiked on a cassette. Residual drug in an infusion line (peristaltic tubing and intravenous tubing) may flow by gravity to a still connected patient when a used cassette, without a vial, is being removed from a pumping unit. Air entrainment may also be possible in such a situation placing a patient at risk of air emboli in the bloodstream.

If an intravenous (IV) set is disconnected at the cassette end after a drug infusion and the same IV set is subsequently used for infusing fluid to the same patient, residual drug trapped in the IV line, between the cassette end and the IV cannula end, will be infused to the patient first. In the case of potent drugs, the residual drug may produce unexpected consequences such as drowsiness and/or loss of consciousness. If the patient has been transported after the drug infusion, for example, for a sedation and analgesia procedure, to another location where no resuscitation personnel or equipment is available and/or functioning, an unplanned clinical emergency may occur that may place the patient at risk.

Most IV infusion tubing sets use a manually-operated slide valve that is placed between a drug container end and an IV cannula end. A user of the infusion system has to remember to manually close the slide valve after an infusion so that free flow of residual drugs potentially followed by air entrainment does not occur upon disconnection of the IV line at the drug container end. If a slide clamp is placed upstream of the IV cannula end, then the slide valve, even if closed, cannot prevent air aspiration upon disconnection of the IV line at the IV cannula (patient) end. Thus, in conventional IV infusion tubing sets, disconnection at the IV cannula end would present a risk of air aspiration resulting in air emboli unless there is another stopcock or flow control component downstream at the IV cannula. A stopcock manufactured from a hard material such as plastic, when in close contact with a patient, may apply under certain circumstances, undue pressure to a patient's skin and tissues resulting in hypoperfusion, nerve injury or tissue damage.

Some drug cassettes incorporate peristaltic tubing held in position next to a rigid pressure plate on the cassette. One end of the peristaltic tubing is in fluid connection to a vial mounted on the drug cassette and the other end of the peristaltic tubing is in fluid connection to intravenous tubing that delivers fluid to a patient. A pumping mechanism, usually external to a drug cassette, presses rhythmically on the peristaltic tubing to pump the vial content and control its flow rate to the patient. The peristaltic tubing has to be held in place against the drug cassette pressure plate for accurate pumping action. In some existing designs, this is done with multiple metal clips that increase parts count.

Another potential failure mode during drug infusion may occur if peristaltic tubing is placed in the reverse orientation relative to a pumping unit, such that blood would be suctioned from a patient instead of drug being delivered to the patient. An indexing mechanism is generally used to prevent peristaltic tubing from being oriented in the reverse direction. This may be, for example, a mechanical part or component attached onto the peristaltic tubing with a corresponding, matching recess in a pumping unit when the peristaltic tubing is properly oriented. If the peristaltic tubing is improperly oriented, the mechanical indexing component will prevent mating of the peristaltic tubing to the drug cassette pressure plate and/or the pumping unit.

Re-use of drug cassettes may lead to cross-contamination by blood-borne pathogens. Prevention of accidental or deliberate re-use of used and contaminated drug cassettes is desirable from the point of view of patient safety.

Current vial entry mechanisms include metal spikes, such as, for example, metal-tipped spikes. Spikes that are designed for use with rigid walled containers like glass vials sometimes have two lumens, one for channeling flow of the vial content to a desired conduit and the other lumen for preventing buildup of vacuum above a meniscus of an inverted vial by allowing equilibration to atmospheric pressure.

Metal, or metal-tipped, spikes generally require less force to pierce a given vial stopper than plastic spikes. For an automated or semi-automated vial spiking system, higher spiking forces usually required by a plastic spike may lead to unreliable spiking action and in case of repeated uses (multiple vials used with a single cassette), high spiking forces may lead to failure of a plastic spike.

If a drug to be infused from a vial is capable of supporting bacterial growth such as the lipid emulsion used in propofol, a filter is used to trap airborne organisms and prevent them from entering into the vial, contaminating the drug, multiplying and harming a patient when the organisms are infused with the drug into the patient's bloodstream. The air filter generally comprises a filter media, a filter media holder and an external filter housing.

BRIEF SUMMARY OF THE INVENTION

The present invention solves the aforementioned drawbacks of and needs from drug infusion devices by providing a drug infusion cassette that incorporates a strong vial spike that may be non-metal, a means for sheathing the spike when it is not in use, an anti-free flow device, and other beneficial features such as an air entrainment lockout mechanism, quality assurance tags, stopcocks made of, or shrouded in, soft materials and means of securing tubing to the cassette with a minimum of individual parts.

More particularly, the present invention provides a drug cassette with a sheathed vial spike made of injection molded plastic with an automated free flow prevention feature. The drug cassette can be used with an automated spiking mechanism comprising a motorized vial holder that holds a vial. The spike remains sheathed if the drug cassette is not fully engaged with a mating surface of devices such as, for example, a pumping unit or a sedation and analgesia delivery system. In general, the vial will be upside down but the invention also contemplates the possibility of having the vial upright. The cassette of the present invention may include molded snap retainers or clips integral to the drug cassette in lieu of metal clips to hold peristaltic tubing in place, thus reducing parts count. A stopcock at the IV cannula or patient end, if present, is made of, or shrouded in, soft materials so that the risk of a pressure-induced injury is reduced.

The present invention also provides a spike that can withstand the repeated stresses of multiple vial spikings and still be made of an inexpensive safe material such as injection molded plastic. Preferably, such a plastic spike of the present invention features a spiking force or peak spiking force that is similar to or less than that of a metal spike. The invention comprises different vial spike geometries, designed for injection molding manufacture, that minimize the force or peak force required to pierce a given vial stopper. An injection molded, sheathed vial spike may be less expensive to produce and easier and cheaper to dispose of, after use than an unsheathed metal or metal-tipped spike. An absence of sharp metal parts may mean that a sheathed, injection-molded spike can be safely discarded in contaminated wastebaskets, instead of a sharps box.

The automated sheathing of the spike when a drug vial is not mounted to the drug cassette minimizes the risk of accidental sharps injury. The design provides tamper-resistant inaccessibility to the spike when the spike is not inserted in a vial, to further minimize risk of accidental sharps injury. When the vial entry mechanism and/or the cassette are made of plastic, the design of those elements is compatible with constraints imposed by injection molded tool design.

In considering the mechanics of inserting a spike or vial entry device or trocar into a vial stopper, the force and/or peak force to insert a spike into a stopper comprises at least three major components: puncturing, tearing and cutting. Puncture is typically defined as a point propagation through a membrane that does not allow the elastic limits of a membrane or stopper to be compromised. Tearing is typically considered as point propagation that exceeds elastic limits. A membrane tears along stress planes (tear propagation) but sealing and multiple puncture characteristics of the membrane are not compromised. Cutting is typically defined as point propagation via a cutting edge before the elastic limits of a material are reached. A larger diameter results in a higher entry force and/or peak entry force, all other parameters being kept constant.

A trocar design that primarily uses puncture and cutting actions will most likely produce low entry force and/or peak entry force. A tearing action requires greater forces due to friction as the trocar surface passes through tear planes. Cut propagation along with minimized cross-sectional area will promote low entry forces. However, cross-sectional area cannot be too small because a vial entry device needs to incorporate one or two lumens with a diameter of, for example, 0.040 inch along its length. A combination of two cutting surfaces at each end of the "stress-strain" points, along with least lateral movement (stretching) of membrane fibers making up a stopper appear to be most effective in reducing entry force and/or peak entry force.

The invention includes a trocar exhibiting one or more than one of the following advantageous features aimed at reducing vial entry force and/or peak entry force: low cross-sectional area, a design that promotes puncture and cutting actions while minimizing lateral movement of membrane fibers, minimal or no tearing actions and a combination of two cutting surfaces at each end of the "stress-strain" points. The rate of change of cross-sectional area (A) with respect to distance from the tip (x) is expressed as dA/dx. Changes in dA/dx should be minimized, for example, no abrupt changes in cross-sectional area. The value of dA/dx should be kept low. A cutting or tearing edge is placed wherever there is a tendency to stretch so that the design promotes cutting and tearing rather than stretching.

Upon removal of a vial from the drug cassette, a spike sheath re-deploys to sheath the spike. The movement of the spike sheath is used to actuate a lever arm that rotates a stopcock such that a drug lumen in a spike assembly is closed and drug flow is prevented. Thus, after a drug infusion, uncontrolled free flow of residual drug left in the peristaltic and intravenous tubing to a patient still connected to the drug cassette is prevented.

A breakable fin on the drug cassette is used as an indicia of the use status of the drug cassette. The air filter housing is incorporated into a spike assembly to reduce parts count. A holder for the air filter media may also be incorporated in the spike assembly to further reduce parts count and manufacturing cost.

The cassette is indexed to its mating surface by designing the cassette such that it can only mount onto its mating surface in one orientation.

BRIEF DESCRIPTION OF THE DRAWINGS

FIG. 1a is a plan view, FIG. 1b is a front view, FIG. 1c is a side view and FIG. 1d is a perspective view of the same trocar design;

FIG. 2a is a plan view, FIG. 2b is a front view, FIG. 2c is a side view and FIG. 2d is a perspective view of the same trocar design;

FIG. 3a is a plan view, FIG. 3b is a front view, FIG. 3c is a side view and FIG. 3d is a perspective view of the same trocar design;

FIG. 4a is a plan view, FIG. 4b is a front view, FIG. 4c is a side view and FIG. 4d is a perspective view of the same trocar design;

FIG. 5a is a plan view, FIG. 5b is a front view, FIG. 5c is a side view and FIG. 5d is a perspective view of the same trocar design;

FIG. 6 represents a trocar design with a football shaped cross-section where FIG. 6a is a plan view, FIG. 6b is a front view, FIG. 6c is a side view and FIG. 6d is a perspective view of the same trocar design;

FIG. 7 represents yet another trocar design where FIG. 7a is a plan view, FIG. 7b is a front view, FIG. 7c is a side view and FIG. 7d is a perspective view of the same trocar design;

FIG. 8a is a plan view, FIG. 8b is a front view, FIG. 8c is a side view and FIG. 8d is a perspective view of the same trocar design;

DETAILED DESCRIPTION OF THE PREFERRED EMBODIMENTS

U.S. patent application Nos. 09/324,759, filed Jun. 3, 1999 and 10/208,184, filed Jul. 31, 2002, both hereby incorporated herein by reference, disclose and enable several embodiments of an infusion administration device having various aspects including a cassette for the transfer of infusion liquid from a sealed drug container to a patient having a rigid pressure plate, a drug flow activation device for initiating the transfer of the infusion liquid from the drug container to the device where the device may be a spike for piercing a resealable stopper of a drug container, free-flow prevention devices, and air-entrainment lockout mechanisms, among other aspects. The embodiments of the trocar and cassette of the present invention as described below are meant to be adapted to work with such a device as well as with most other automated liquid infusion devices.

The different spike designs described below may be manufactured of plastic by injection molding. The plastic may be subsequently hardened by annealing or other processes used to harden or cure plastic.

In spike designs where lumen openings at or near a spike tip are at different elevations, the upper lumen opening may preferably be used for venting while the lower lumen opening may preferably be used for channeling the content of a spiked container. This ensures less wastage of the infusion liquid by increasing the amount of liquid in a vial that can be infused before the meniscus gets too close to the drug flow lumen opening. That is, a lower lumen opening will keep on channeling the vial content if the meniscus is below an upper lumen opening and above the lower lumen opening. Conversely, a higher lumen opening might preferably be used for an atmospheric vent so that the atmospheric vent is beneath the infusion liquid meniscus for a shorter time.

The lumens are shown in FIGS. 1–8 as circular lumens because circular lumens may be easier to injection mold but the lumens do not necessarily need to be circular. They could instead be oval or some other non-circular shape that minimizes the aspect ratio, area or profile of the spike cross-section. The lumens do not necessarily need to each be of the same diameter and/or shape as they accomplish different functions. A venting lumen channels air into a vial to relieve vacuum while a drug flow lumen channels liquid content out of the vial.

The bevels are shown as plane surfaces in FIGS. 1–8 but could also be concave and/or convex surfaces in all the different designs described below. Reduction of the cross-sectional area by removing features such as pointed edges from a football shape and replacing them with blunter semi-circles does not seem to reduce the peak vial entry force even though the overall cross-sectional area has been decreased. The peak entry force appears to occur at the point of maximum spread or stretching of the stopper material.

Figure 1:
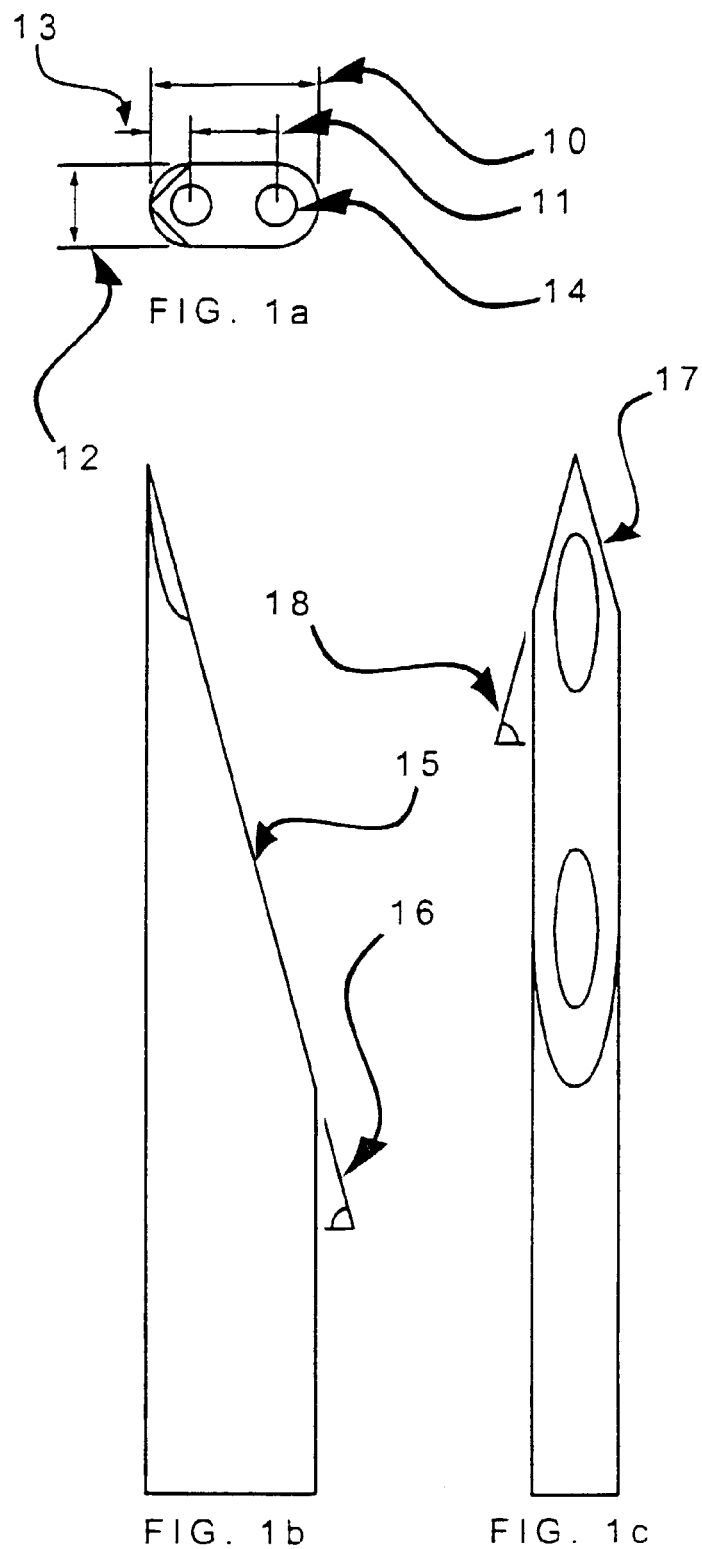
FIG. 1 represents a trocar design where
Figure 1:
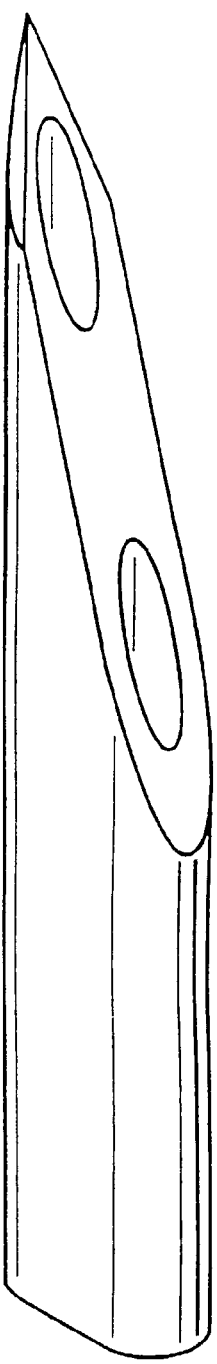

FIG. 1 shows a spike or trocar design with a cross-sectional shape that looks like an athletic track (a rectangle with equal semi-circles replacing two opposite sides of the rectangle). The cross-section shown in FIG. 1a is large enough to accommodate one or more lumens 14, e.g., of 0.03"–0.04" diameter. The lumens 14 do not need to be of equal diameter and/or shape although they are shown with identical diameters and shapes. If two lumens are present, the centers of the lumens have a spacing 11, which may, for example, be in the range between 0.06"–0.08". The cross-section of the spike has a thickness 12, which may, for example, be 0.08" wide with the centers for the 0.08" diameter semi-circles spaced for example, 0.06"–0.08" apart. The centers of the lumens and the semi-circles happen to be coincident in FIG. 1a but do not necessarily need to be so. The cross-section has a width 10 which may, for example, be in the range of 0.14"–0.16". In FIG. 1a, the center of the left lumen is at a distance 13 from the left edge of the cross-section where 13 may, for example, be 0.04". The centers of the lumens 14 do not necessarily need to be symmetrically laid onto the cross-section of the spike but may instead be offset. The cross-section does not necessarily need to be symmetrical. For example, the semi-circle on the right side of FIG. 1a may have a different diameter than that on the left side. Similarly, the top and bottom sides of the shape shown in FIG. 1a do not necessarily need to be parallel but could instead produce a taper (see, for example, FIG. 3a).

The spike has a bevel 15 across its entire cross-section at an angle 16 from the horizontal (FIG. 1b). For example, the bevel angle 16 could be 70°–80° with the actual angle shown in FIG. 1b being 75°. Additional bevels 17 at an angle 18 to the horizontal may be added at the tip to provide a sharper point to the spike tip (FIG. 1e). The angle 18 may be, for example, 70°–80° with the actual angle shown in FIG. 1c being 75°. The additional bevels 17 may or may not join together at the tip and may not necessarily be symmetrical. In FIG. 1c, the bevels 17 are shown as symmetrical and joining at the tip. Bevel 15 is shown as a non-skewed cut in FIG. 1, in the sense that corresponding points on the top and bottom straight edges in FIG. 1a are at the same elevation when the spike is upright or vertical. Bevel 15 may be skewed, instead of level, such that FIG. 1c becomes asymmetric even if the cross-section in FIG. 1a is symmetrical.

Figure 2:
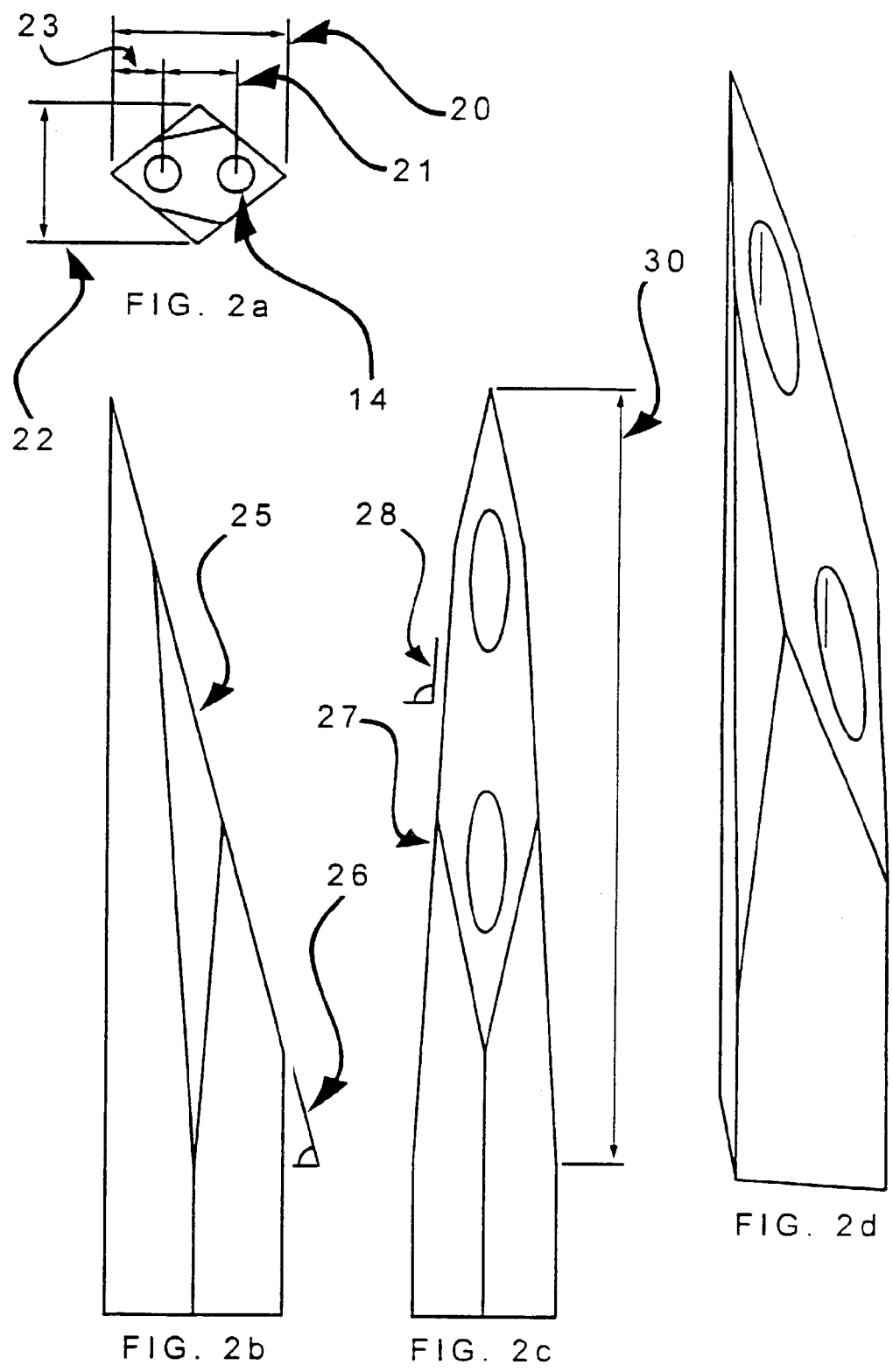
FIG. 2 represents a trocar design with a diamond cross-section where

FIG. 2 represents an alternative spike design with a diamond cross-section incorporating one or more lumens 14, e.g., of 0.03"–0.04" diameter. The lumens 14 do not need to be of equal diameter and/or shape although they are shown with identical diameters and shapes. If two lumens 14 are present, the centers of the lumens have a spacing 21, which may, for example, be 0.07"–0.08" along the shorter axis 22. Alternatively, the centers of the two lumens may be aligned along the long axis 20 as shown in FIG. 2a. The shorter axis 22 maybe, for example 0.15" long and the longer axis 20 maybe, for example, 0.188" long. In some embodiments of the design, the long axis 20 and the short axis 22 may be identical such that the diamond cross-section becomes a square cross-section. In FIG. 2a, the center of the left lumen is at a distance 23 from the left edge of the cross-section where 23 may, for example, be 0.054". The centers of the lumens 14 do not necessarily need to be symmetrically laid onto the cross-section of the spike but may instead be offset. The diamond cross-section does not necessarily need to be symmetrical. For example, the pointed edge on the right side of FIG. 2a may be at a different angle and distance from the centerline compared to the left edge.

A large bevel 25 across the entire cross-section at an angle 26 from the horizontal, in combination with the diamond cross-section, produces the spike tip (FIG. 2b). For example, the angle 26 may be 70°–80° with the actual angle shown in FIG. 2b being 75°. Additional bevels 27 at an angle 28 to the horizontal, may be added at the sides of the spike (FIG. 2c). The angle 28 may be, for example, 91°–95° with the actual angle shown in FIG. 2c being 93°. The bevels 27 are started at a distance 30 from the tip of the spike. Distance 30 may be, for example, 0.827". The additional bevels 27 may or may not join together at the tip and may not necessarily be symmetrical. In FIG. 2c, the bevels 27 are shown as symmetrical but not joining at the tip. Bevel 25 is shown as a non-skewed cut in FIG. 2. Bevel 25 may be skewed, instead of level, such that FIG. 2c becomes asymmetric even if the cross-section in FIG. 2a is symmetrical.

Figure 3:
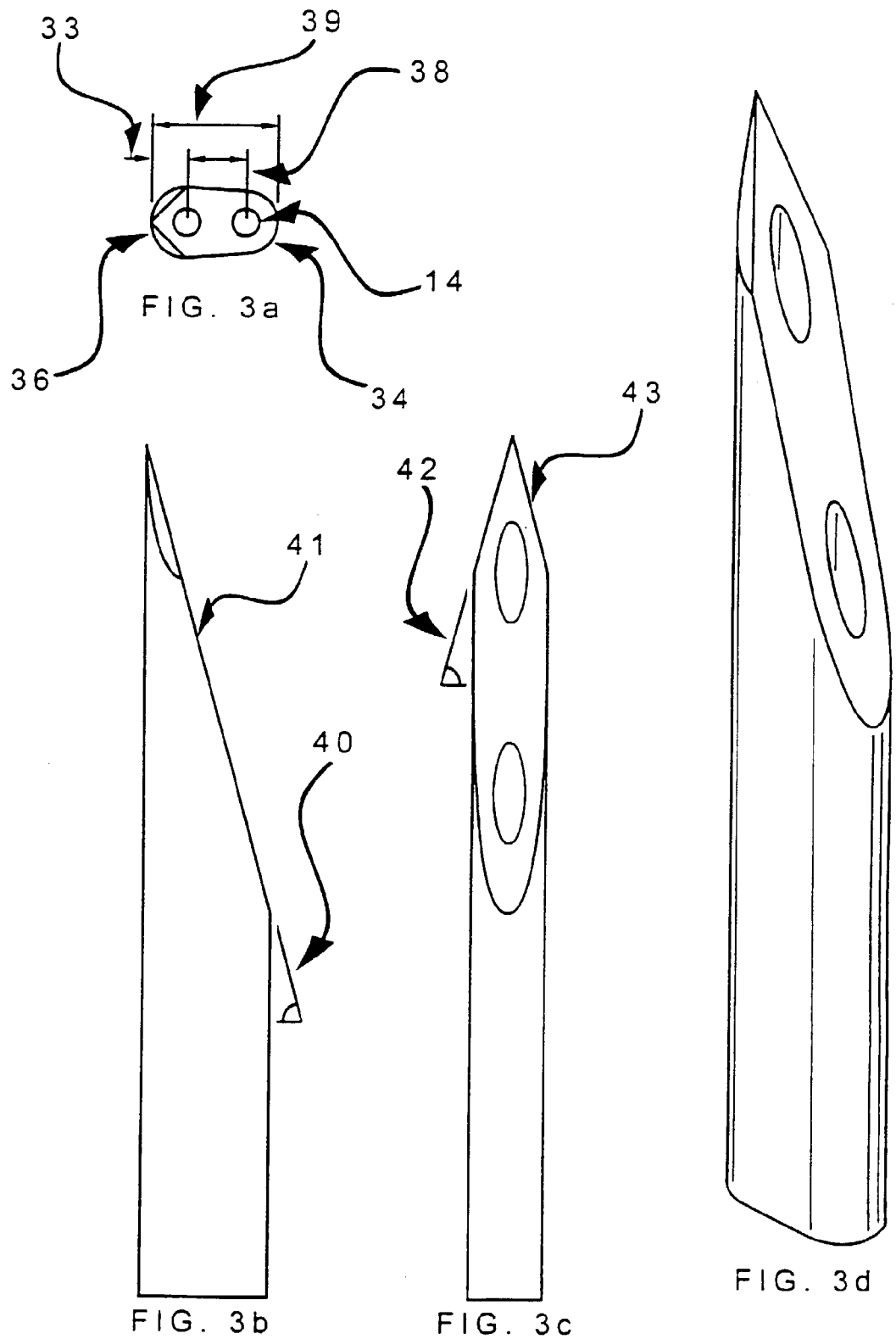
FIG. 3 represents an alternative embodiment of a trocar design where

FIG. 3 represents yet another alternative spike design with a cross-section incorporating one or more lumens 14, e.g., of 0.03"–0.04" diameter, where the short ends of a trapezoid are replaced by semi-circles 34, 36 of unequal diameter. The lumens 14 do not need to be of equal diameter and/or shape although they are shown with identical diameters and shapes. If two lumens 14 are present, the centers of the lumens have a spacing 38 which may, for example, be 0.065". One semi-circle 36 may be, for example, of 0.08" diameter with the other semi-circle 34 at, for example, 0.07" diameter (FIG. 3a). The entire width 39 of the cross-section maybe, for example, 0.14". The lumen at the narrower semi-circle 34 may be narrower, e.g., of 0.03" diameter. The distance 33 from the center of the left lumen to the left edge in FIG. 3a may, for example, be 0.04". The centers of the lumens 14 do not necessarily need to be symmetrically laid onto the cross-section of the spike but may instead be offset. The centers of the lumens 14 and the semi-circles 34, 36 happen to be coincident in FIG. 3a but do not necessarily need to be so.

A large bevel 41 at an angle 40 to the horizontal is made across the entire cross-section (FIG. 3b). For example, the bevel angle 40 may be 70°–80° with the actual angle shown in FIG. 3b being 75°. Additional bevels 43 at an angle 42 to the horizontal may be added at the tip to provide a sharper point to the spike tip (FIG. 3c). The angle 42 may be, for example, 70°–80° with the actual angle shown in FIG. 3c being 75°. The additional bevels 43 may or may not join together at the tip and may not necessarily be symmetrical. In FIG. 3c, the bevels 43 are shown as symmetrical and joining at the tip. Bevel 41 is shown as a non-skewed cut in FIG. 3, in the sense that corresponding points on the top and bottom edges in FIG. 3a are at the same elevation when the spike is upright or vertical. Bevel 41 may be skewed, instead of level, such that FIG. 3c becomes asymmetric even if the cross-section in FIG. 3a is symmetrical.

Figure 4:
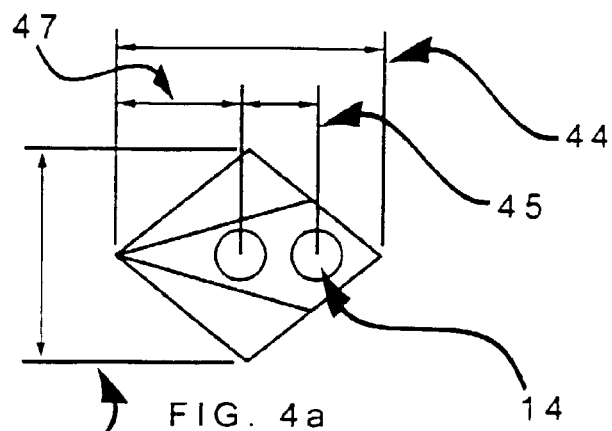
FIG. 4 represents a trocar design with a diamond cross-section where
Figure 4:
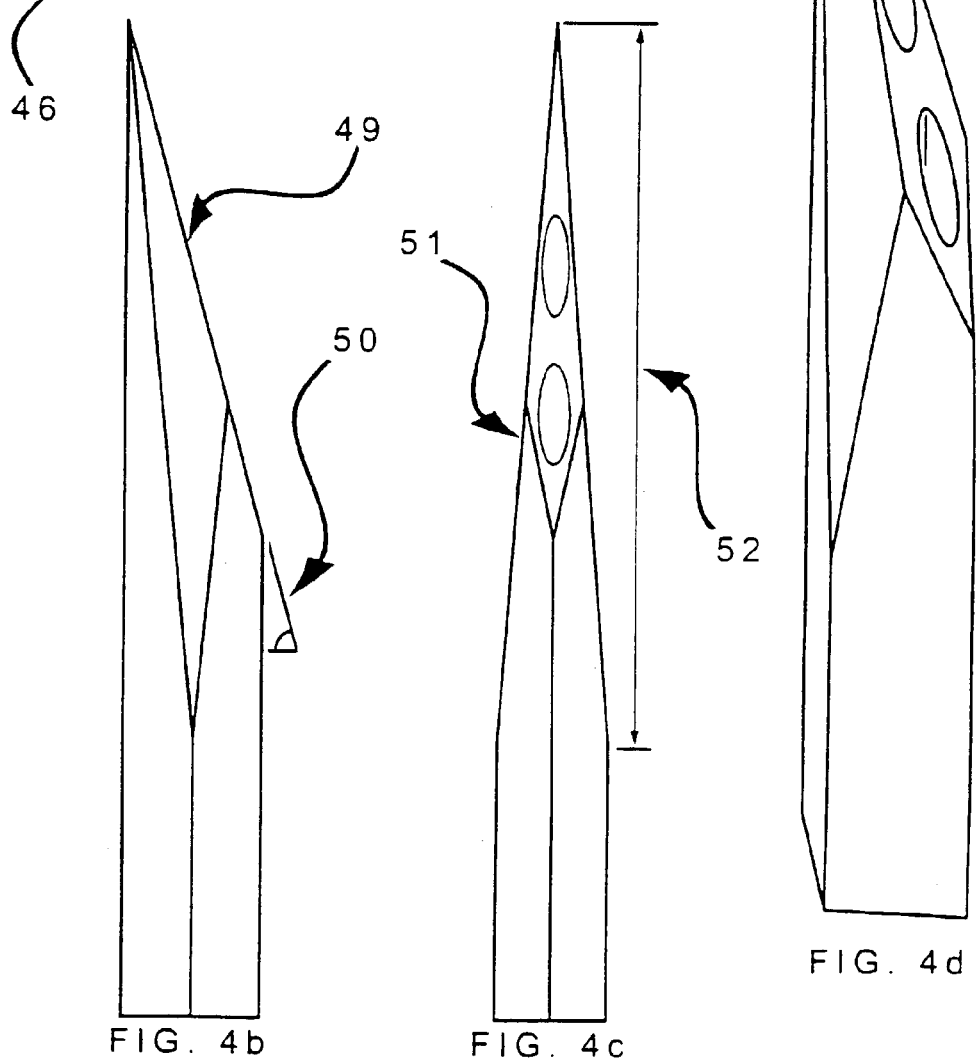

FIG. 4 represents still another spike design with a diamond cross-section incorporating one or more lumens 14, e.g., of 0.03"–0.04" diameter. The lumens 14 do not need to be of equal diameter and/or shape although they are shown with identical diameters and shapes. If two lumens are present, the centers of the lumens have a spacing 45, which may, for example, be 0.08" apart along the shorter axis 46. The shorter axis 46 may be, for example 0.16" long and the longer axis 44 may be, for example, 0.2" long. In some embodiments of the design, the long axis 44 and the short axis 46 may be identical such that the diamond cross-section becomes a square cross-section. The centers of the lumens may also be aligned along the long axis 44 as shown in FIG. 4a and the distance 45 between the lumen centers may be, for example, 0.057". The distance 47 from the center of the left lumen to the left edge in FIG. 4a may, for example, be 0.094". The centers of the lumens 14 do not necessarily need to be symmetrically laid onto the cross-section of the spike but may instead be offset. In FIG. 4a, the lumens are purposely offset to the right so that the intersection of the lumens with the bevels 49 and 51 do not create "hooks" on which the stopper material might snag, thus generating or requiring a higher vial entry force. The diamond cross-section does not necessarily need to be symmetrical. For example, the pointed edge on the right side of FIG. 4a may be at a different angle and distance from the centerline compared to the left edge.

A large bevel 49 at an angle 50 to the horizontal is made across the entire cross-section (FIG. 4b). For example, the bevel angle 50 may be 70°–80° with the actual angle shown in FIG. 1c being 75°. Additional bevels 51 may be added starting at a distance 52 from the tip and joining together at the tip to provide a sharper point to the spike tip (FIG. 4c). Distance 52 may, for example, be 1.051". The additional bevels 51 may or may not join together at the tip and may not necessarily be symmetrical. In FIG. 3c, the bevels 51 are shown as symmetrical and joining at the tip. Bevel 49 is shown as a non-skewed cut in FIG. 4. Bevel 49 may be skewed, instead of level, such that FIG. 4c becomes asymmetric even if the cross-section in FIG. 4a is symmetrical.

Figure 5:
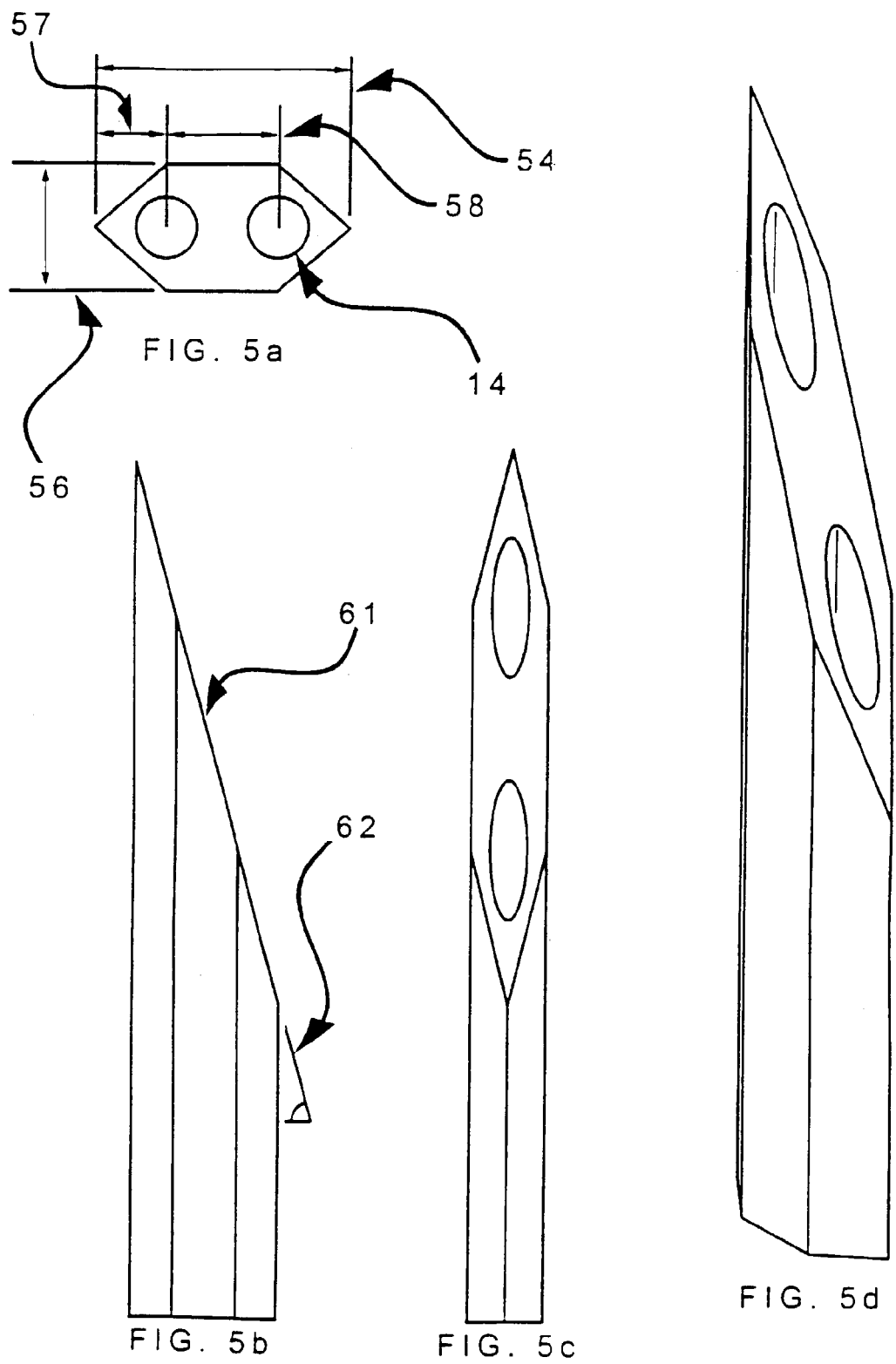
FIG. 5 represents a trocar design with a stretched hexagon cross-section where

FIG. 5 depicts a spike with a stretched hexagonal cross-section incorporating one or more lumens 14, e.g., of 0.03"–0.04" diameter. The lumens 14 do not need to be of equal diameter and/or shape although they are shown with identical diameters and shapes (FIG. 5a). If two lumens are present, the centers of the lumens have a spacing 58, which may be, for example, 0.07" along the long axis 54. The short axis 56 of the hexagon may be, for example, 0.08" long and the long side or axis 54 may be, for example, 0.16" long. The distance 57 from the center of the left lumen to the left edge in FIG. 5a may, for example, be 0.045". The centers of the lumens 14 do not necessarily need to be symmetrically laid onto the cross-section of the spike but may instead be offset. The stretched hexagonal cross-section does not necessarily need to be symmetrical. For example, the pointed edge on the right side of FIG. 5a may be at a different angle and distance from the centerline compared to that on the left side. Similarly, the top and bottom sides of the hexagon shown in FIG. 5a do not necessarily need to be parallel but could instead produce a taper.

A large bevel 61 at an angle 62 to the horizontal, is made across the entire cross-section (FIG. 5b). For example, the angle 62 may be, for example, 70°–80° with the actual angle shown in FIG. 5b being 75°. Bevel 61 is shown as a non-skewed cut in FIG. 5, in the sense that corresponding points on the top and bottom straight edges in FIG. 5a are at the same elevation when the spike is upright or vertical. Bevel 61 may be skewed, instead of level, such that FIG. 5c becomes asymmetric even if the cross-section in FIG. 5a is symmetrical.

FIG. 6 illustrates a spike with a football shaped cross-section incorporating one or more lumens 14, e.g., of 0.03"–0.04" diameter. The lumens 14 do not need to be of equal diameter and/or shape although they are shown with identical diameters and shapes (FIG. 6a). If two lumens are present, the centers of the lumens 14 have a spacing 65, which may, for example, be 0.07" apart along the long axis 64 which may, for example, be 0.188" long. The thickness 66 of the cross-section may, for example, be 0.05"–0.08". The distance 67 from the center of the left lumen to the left edge in FIG. 6a may, for example, be 0.059". The centers of the lumens 14 do not necessarily need to be symmetrically laid onto the cross-section of the spike but may instead be offset. The football shaped cross-section does not necessarily need to be symmetrical. For example, the pointed edge on the right side of FIG. 6a may be at a different angle and at a different distance from the midline compared to the left side. Similarly, the top and bottom sides of the football shape shown in FIG. 6a do not necessarily need to be symmetrical but could instead have different radii.

A large bevel 69 at an angle 70 to the horizontal across the entire cross-section is used to generate the tip (FIG. 6b). For example, angle 70 may be 70°–80° with the actual angle shown in FIG. 6b being 75°. Bevel 69 is shown as a non-skewed cut in FIG. 6, in the sense that corresponding points on the top and bottom edges in FIG. 6a are at the same elevation when the spike is upright or vertical. Bevel 69 may be skewed, instead of level, such that FIG. 6c becomes asymmetric even if the cross-section in FIG. 6a is symmetrical.

FIG. 7 is a graphical representation of a spike with a cross-sectional shape that looks like an athletic track (a rectangle with a semi-circle replacing each short end). The cross-section is large enough to accommodate one or more lumens 14, e.g., of 0.03"–0.04" diameter. The lumens 14 do not need to be of equal diameter and/or shape although they are shown with identical diameters and shapes (FIG. 7a). If two lumens are present, the centers of the lumens have a spacing 75, which may be, for example, 0.07". The cross-section of the spike has a thickness 76, which may, for example, be 0.08" with the centers for the semi-circles spaced, for example, 0.07" apart. The centers of the lumens and the semi-circles happen to be coincident in FIG. 7a but do not necessarily need to be so. The long axis 74 may be, for example, 0.15" long. In FIG. 7a, the center of the left lumen is at a distance 77 from the left edge of the cross-section where 77 may, for example, be 0.04". The centers of the lumens 14 do not necessarily need to be symmetrically laid onto the cross-section of the spike but may instead be offset. The cross-section does not necessarily need to be symmetrical. For example, the semi-circle on the right side of FIG. 7a may have a different diameter than that on the left side. Similarly, the top and bottom sides of the shape shown in FIG. 7a do not necessarily need to be parallel but could instead produce a taper (see, for example, FIG. 3a).

Two symmetrical bevels 79 join at the midline to form a tip at an angle 80 to the horizontal (FIG. 7b) and generate a line at an angle 82 to the horizontal (FIG. 7c). Angle 80 might be, for example, 60°–70° whereas angle 82 might be 65°. Bevels 79 are shown as symmetrical but do not necessarily need to be so.

Figure 8:
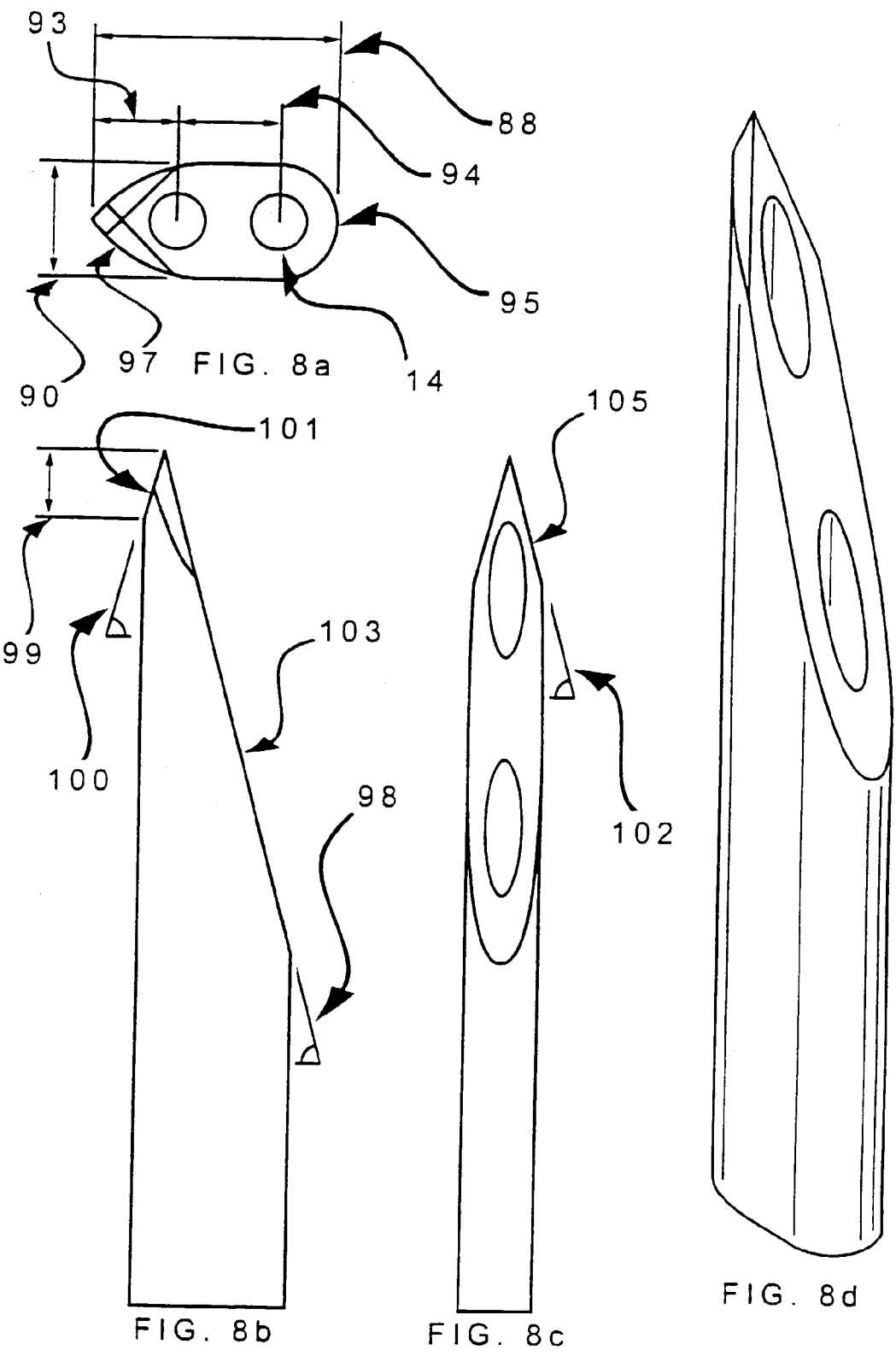
FIG. 8 represents a trocar design with an ogival cross-section where

FIG. 8 is a drawing of a spike design with a semi-ogival cross-section with a thickness 90 and a width 88. A semi-circle 95 which may be, for example, of 0.08" diameter is at one end of the cross-section. The other end of the cross-section is composed of an ogive 97. Thickness 90 may be, for example, 0.08". The long axis or width 88 of the cross-section may be, for example, 0.169" long (FIG. 8a). Ogive 97 may be for example, 0.08" thick and 0.094" long when measured from the midpoint between the two lumen centers. The two curves of the ogive 97 are composed of segments of circles with a radius of, for example, 0.104".

The ogive 97, although shown as symmetrical does not necessarily need to be symmetrical. The two curves of the ogive 97 could be from segments of circles of different radii. The cross-section is large enough to accommodate one or more lumens 14, e.g., of 0.03"–0.04" diameter. The lumens 14 do not need to be of equal diameter and/or shape although they are shown with identical diameters and shapes (FIG. 8a). If two lumens are present, the centers of the lumens have a spacing 94, which may, for example, be 0.07". In FIG. 8a, the center of the left lumen is at a distance 93 from the left edge of the cross-section where 93 may, for example, be 0.059". The centers of the lumens 14 do not necessarily need to be symmetrically laid onto the cross-section of the spike but may instead be offset. The cross-section does not necessarily need to be symmetrical. For example, the middle of the top and bottom sides of the shape shown in FIG. 8a do not necessarily need to be parallel but could instead produce a taper.

A large bevel 103 at an angle 98 to the horizontal and another smaller bevel 101 at an angle 100 to the horizontal combine to make a point (FIG. 8b). The bevel angles 98, 100 may, for example, be equal at 70°–80° but may also be of unequal values. The actual bevel angle 98, 100 shown in FIG. 8b is 75°. The smaller bevel 101 may start, for example, at a distance 99 from the tip, which may, for example, be 0.075". Two small additional bevels 105 at an angle 102 to the horizontal are used to generate a sharper tip. Angle 102 may be, for example, 70°–80° with the actual angle shown being 75°. The bevels 105 may or may not be symmetrical even though they are shown as symmetrical in FIG. 8c. Bevels 101, 103 are shown as non-skewed cuts in FIG. 8, in the sense that corresponding points on the top and bottom edges in FIG. 8a are at the same elevation when the spike is upright or vertical. Bevels 101, 103 may be skewed, instead of level, such that FIG. 8c becomes asymmetric even if the cross-section in FIG. 8a is symmetrical.

The large bevel 103 by itself would have been sufficient to create a sharp pointed tip when intersecting with the cross-section in FIG. 8a. However, the tip might then be too thin and pointy and might be susceptible to bending and breakage. A smaller bevel, like bevel 101, opposed to bevel 103, serves to make the tip stronger and less susceptible to bending.

Figure 9:
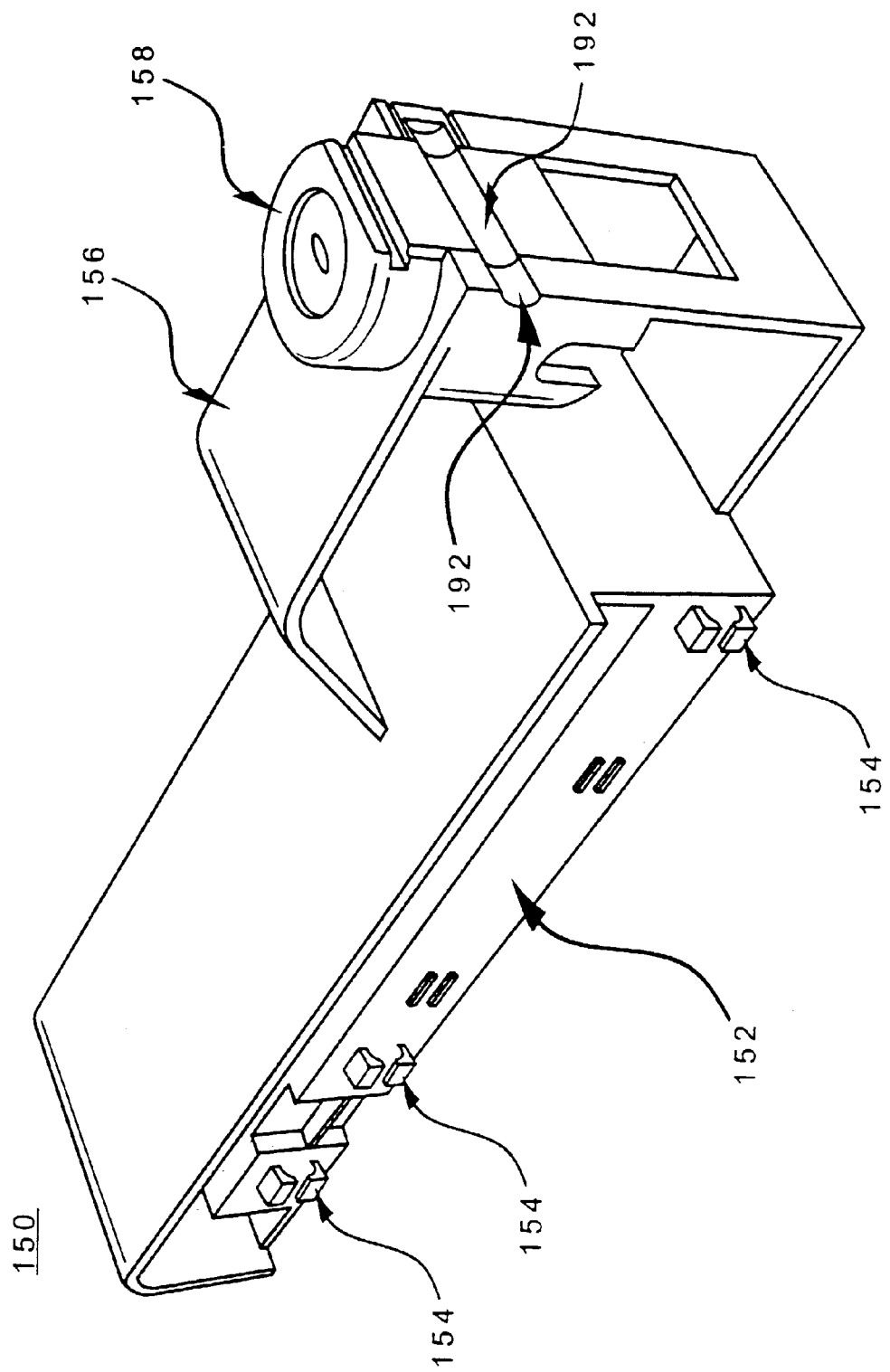
FIG. 9 depicts a perspective view of a drug cassette with integral spike sheathing and anti-free flow features.

FIG. 9 shows a perspective view of a particular embodiment of a drug cassette 150 according to the present invention having a pressure plate 152. Pressure plate 152 may include molded snap retainers 154 or other such means of holding peristaltic tubing (not shown for clarity) in place against the plate. A peristaltic pumping mechanism may be provided with the device that contacts the tubing and works on it against the pressure plate. Cassette body 156 may contain a cavity 176 (shown in FIG. 11) that receives a slidably mounted spike sheath 158 that is shown in a deployed position in FIG. 9. Spike body 156 is constructed so as to allow spike sheath 158 to slide down and expose a spike 163 if drug cassette 150 is fully engaged with mating surface 200 (FIG. 14) of the device and is also constructed so as to not allow sheath 158 to slide down if cassette 150 is not fully engaged with surface 200. In particular embodiments of this invention, then, when a new or used drug cassette 150 is not mounted to mating surface 200, vial sheath 158 will always be deployed to sheath spike 163 and prevent accidental sharps injury. The cassette 150 may then be disposed in a contaminated wastebasket after use with minimized concern about a potential for accidental sharps injury by an exposed spike. A groove 192 may be included on both spike sheath 158 and cassette body 156 to provide clearance for peg 202 of surface 200 that fits into groove 192. A breakable fin may be provided on cassette 150 to act as an indicia of use status of drug cassette 150. The top of drug cassette 150 may be constructed with contoured ridges that provide a better grip for handling the cassette.

Figure 10:
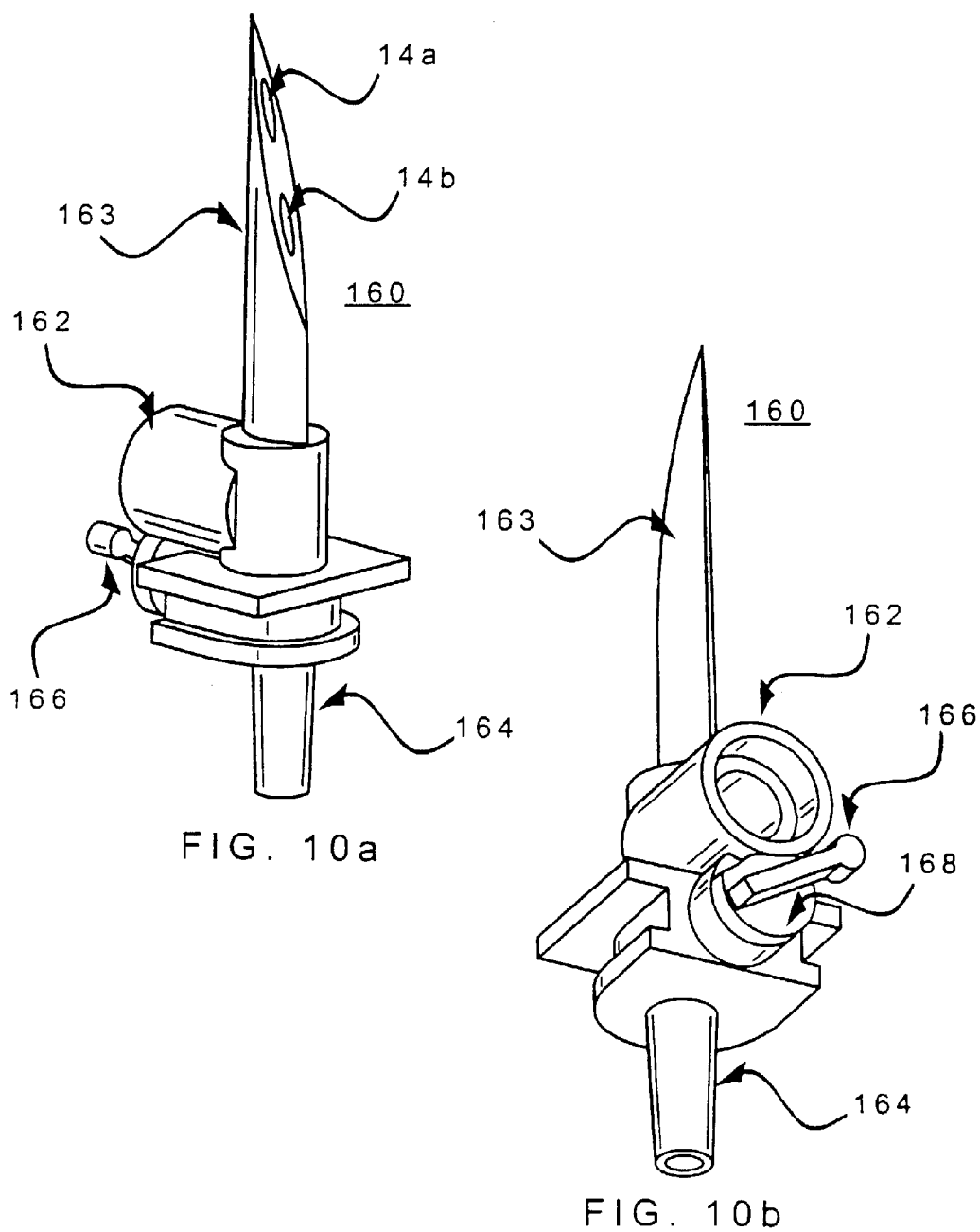
FIGS. 10a and 10b show different perspective views of a spike assembly with an integrated stopcock lever arm that interacts with a drug cassette.

FIG. 10a is a perspective view of an embodiment of a spike assembly 160 which may be fitted to cassette 158 and to the peristaltic tubing. Spike assembly 160 includes spike 163 and may include any or all of air filter housing 162, tapered outlet connector 164 for connection to the peristaltic tubing and lever arm 166 or other means for actuating a stopcock 168 (FIG. 10b). Spike 163 may include lumens 14a (air venting lumen) and 14b (drug flow lumen). Air flows via lumen 14a into a vial when placed over spike assembly 160 and spiked. This air flow may prevent vacuum buildup inside a vial when the vial contents are emptied during infusion. Air filter housing 162 may house a filter element (not shown) that filters out airborne disease organisms from the ambient air that flows into the vial via lumen 14a. Air filter housing 162 may be designed so as to eliminate the use of an air filter media holder that is traditionally used to contain the air filter media, further reducing parts count and cost of manufacture for the apparatus of the present invention. When lever arm 166 is in the up position as is shown in FIGS. 10a and 10b, stopcock 168 is rotated such that drug lumen 14b is closed. A closed drug lumen 14b prevents free flow of residual drug left in peristaltic and intravenous set tubing and prevents potential entrainment of air emboli into the patient's bloodstream in situations where a used drug cassette 150 is removed from mating surface 200 while the intravenous set tubing is still connected to a patient. Spike 163 is shown as one particular shape in the spike assembly figures but may be of any shape, including those described in FIGS. 1–8.

Figure 11:
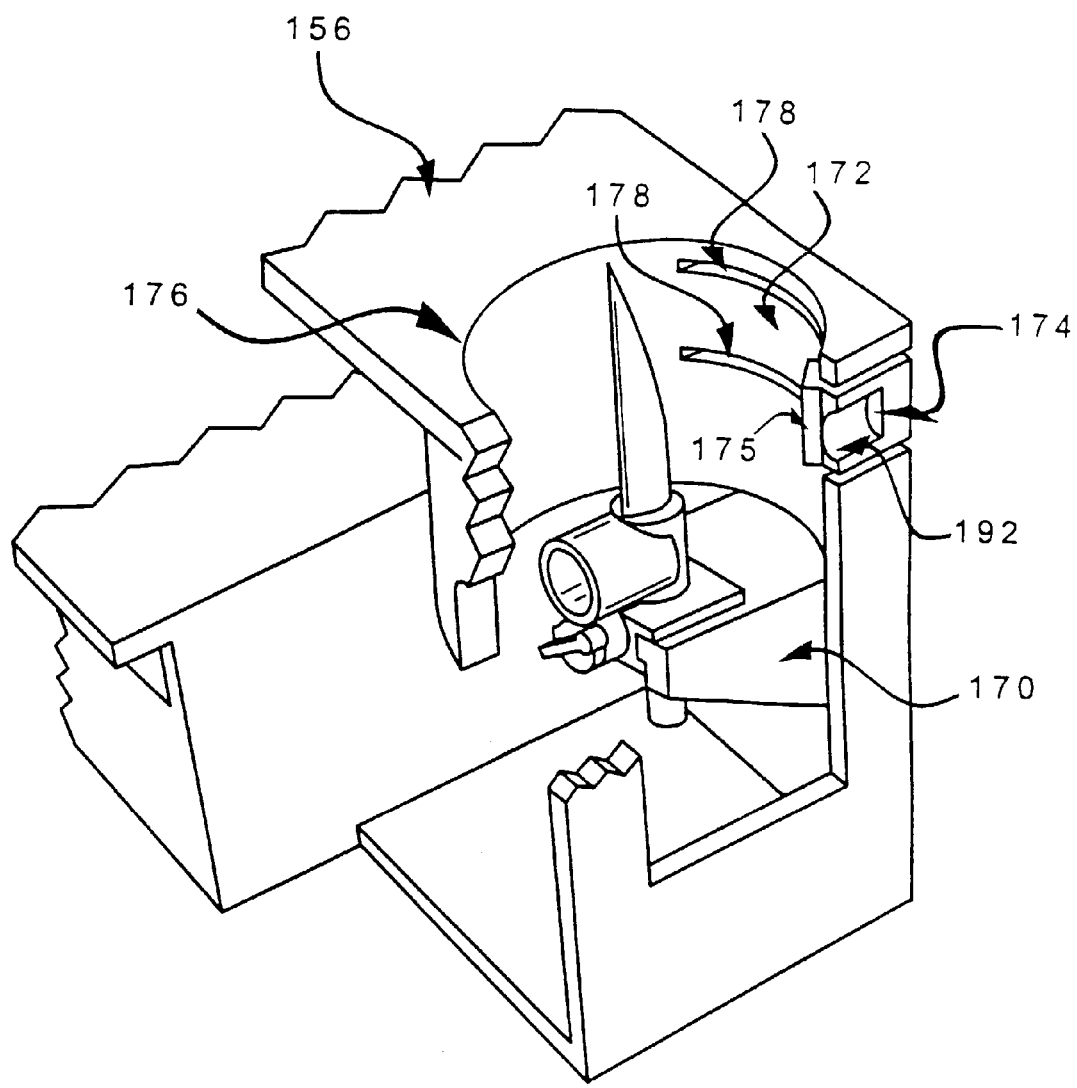
FIG. 11 is a cut-out view of a spike assembly attached to a drug cassette with a spike sheath omitted.

FIG. 11 depicts a cut-out perspective view of drug cassette body 156 with spike sheath 158 removed. A cavity 176 in drug cassette body 156 is designed to accept spike sheath 158 (not shown). Spike assembly 160 (FIG. 10) is attached to a mounting flange 170 which is incorporated in or itself attached to drug cassette body 156. Mounting flange 170 holds spike assembly 160 stationary relative to drug cassette body 156, especially along a vertical axis such that a vial may be pushed onto spike assembly 160. A movable member 172 forms part of the wall of cavity 176 and may be made movable by slits 178 cut below and above member 172. Member 172 may have a groove 192 having end 174. Peg 175 on movable member 172 engages with a notch 184 or other surface of spike sheath 158. Movable member 172, when in a normal resting, or retracted, position, engages notch 184 (FIGS. 14 and 15) in spike sheath 158 with peg 175 thereby preventing vertical movement of spike sheath 158. When movable member 172 is in a deployed position, peg 175 no longer engages notch 184 (FIG. 16), thereby allowing vertical displacement of spike sheath 158. Movable member 172 is deployed when drug cassette 150 is substantially engaged with mating surface 200. A peg 202 may be mounted on mating surface 200 in a position so as to deploy movable member 172 by pushing on end 174 of groove 192, when cassette 150 is placed against mating surface 200.

Vertical displacement of spike sheath 158 allows for each or both of the sheathing and unsheathing of spike 163 and the activation or deactivation of an anti-free flow device. For example, when sheath 158 is in an up position, spike 163 is sheathed by spike sheath 158 and a stopcock 168 is closed thereby preventing free flow of infusion liquid through spike assembly 160. When sheath 158 is in a down position, spike 163 is unsheathed and stopcock 168 is open thereby allowing the flow of infusion liquid through the spike assembly 160.

Figure 12:
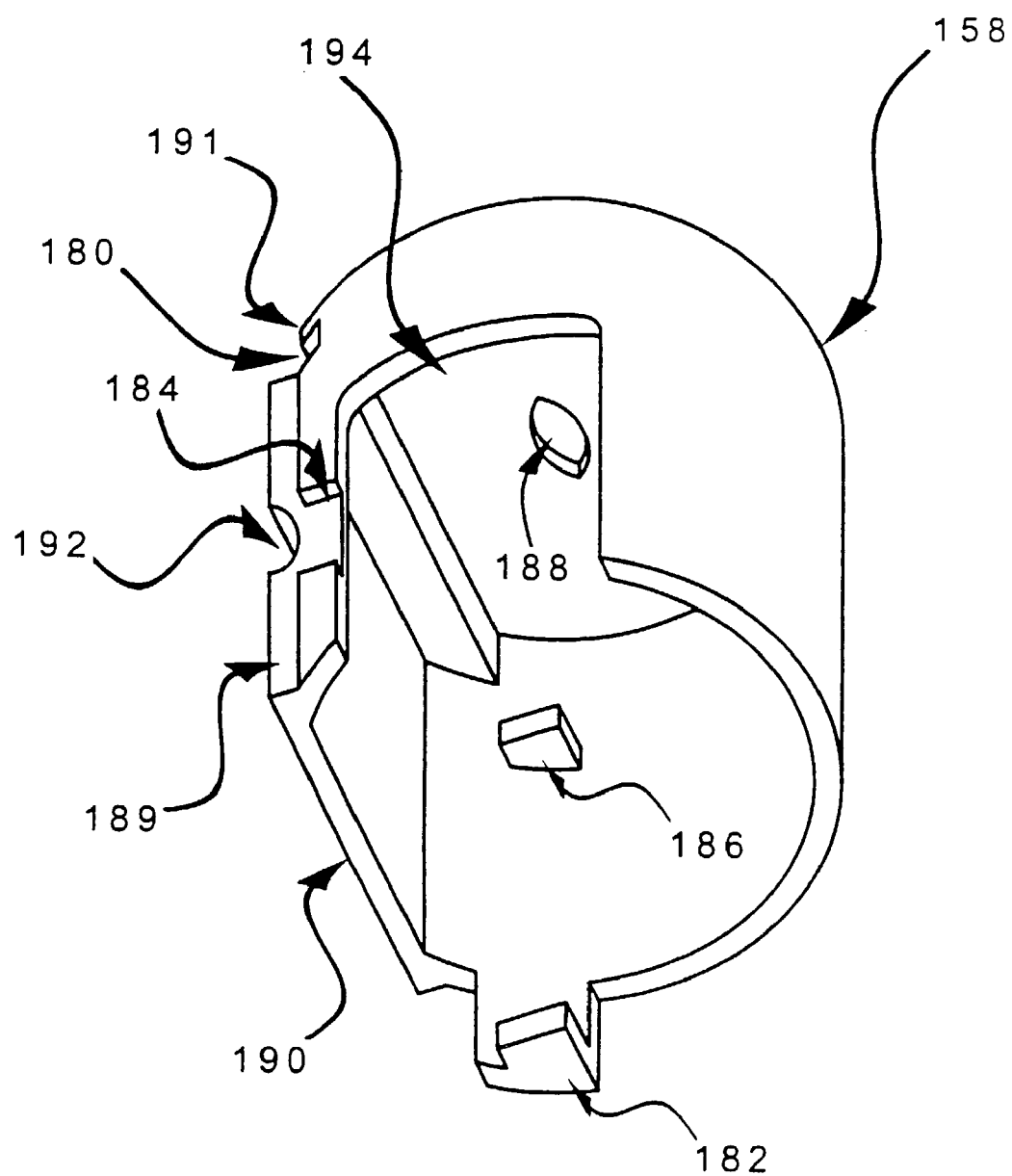
FIG. 12 is a perspective bottom view of a spike sheath.
Figure 13:
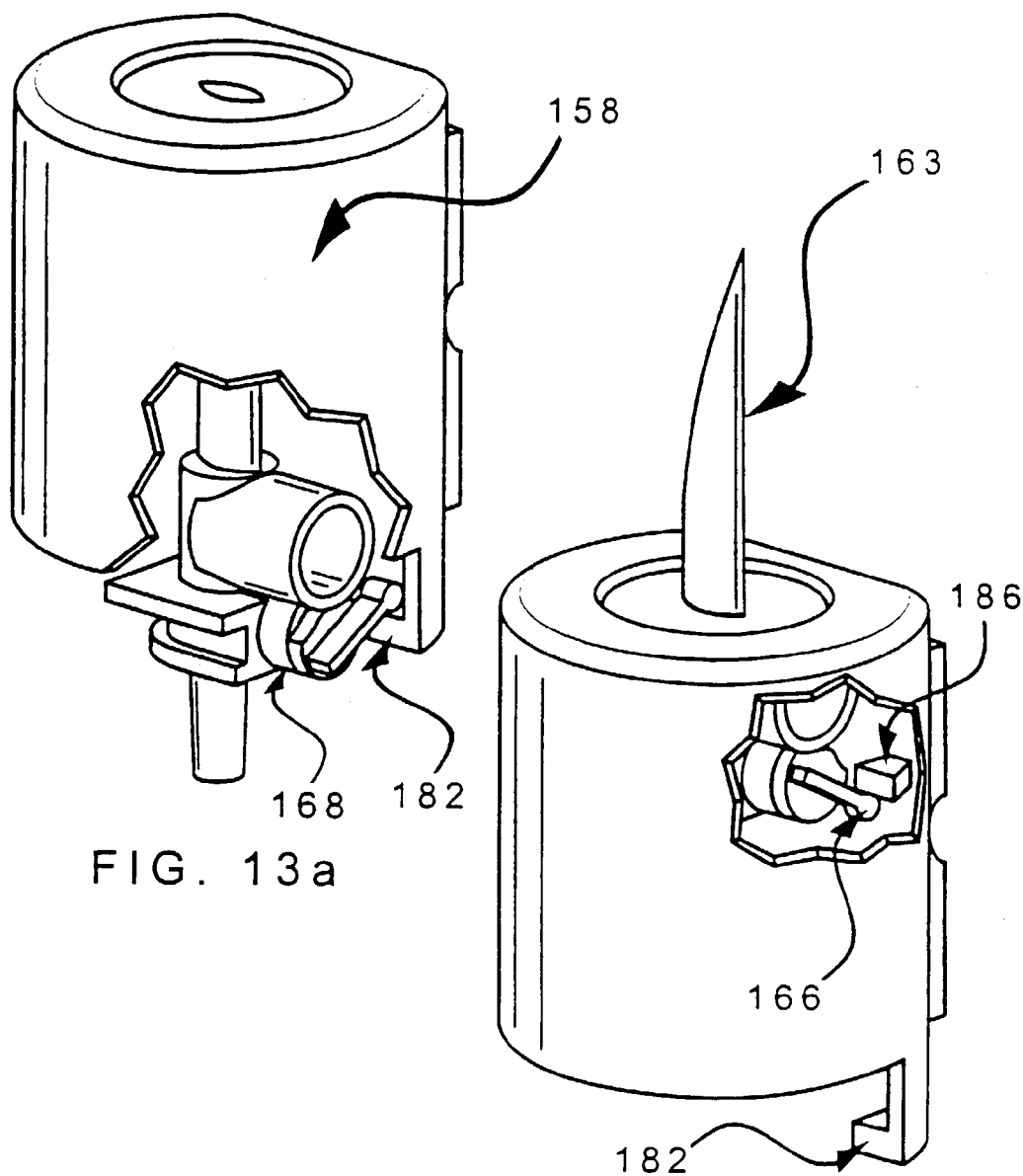
FIGS. 13a and 13b represent perspective cut-out views of an anti-free flow device on a spike assembly interacting with protuberances on a spike sheath, in sheathed and exposed positions respectively.

FIG. 12 shows a perspective view of spike sheath 158 which may include portion 190, opening 188 to let spike 163 go through spike sheath 158 and protuberances 182 and 186 that engage with lever arm 166 to close and open stopcock 168 respectively as spike sheath 158 travels up and down (FIGS. 13a and 13b). At the top of portion 190, a step 180 may be provided with a lip 191 that engages with a vial holder (not shown).

In a particular embodiment, the vial holder engages with step 180 and lip 191 of spike sheath 158 as cassette 150 is engaged to mating surface 200. As movable member 172 is deployed to allow downwards travel of spike sheath 158, the vial holder engages with spike sheath 158 to prevent unplanned downwards travel of spike sheath 158. When the vial holder and spike sheath are interlocked, the spike sheath cannot travel down if the vial holder is not traveling down. Therefore, in such an embodiment, it is not possible to manually depress the spike sheath and expose the spike, when the cassette is fully engaged to its mating surface.

Figure 14:
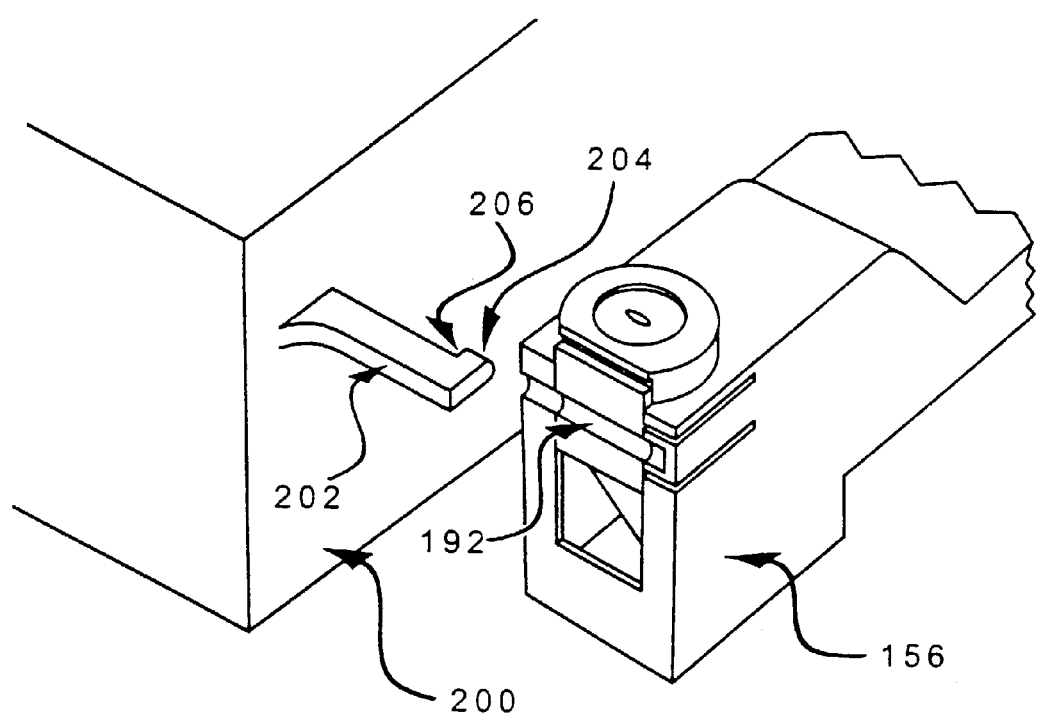
FIG. 14 shows a perspective view of a drug cassette and a mating surface when the two are not yet touching.
Figure 15:
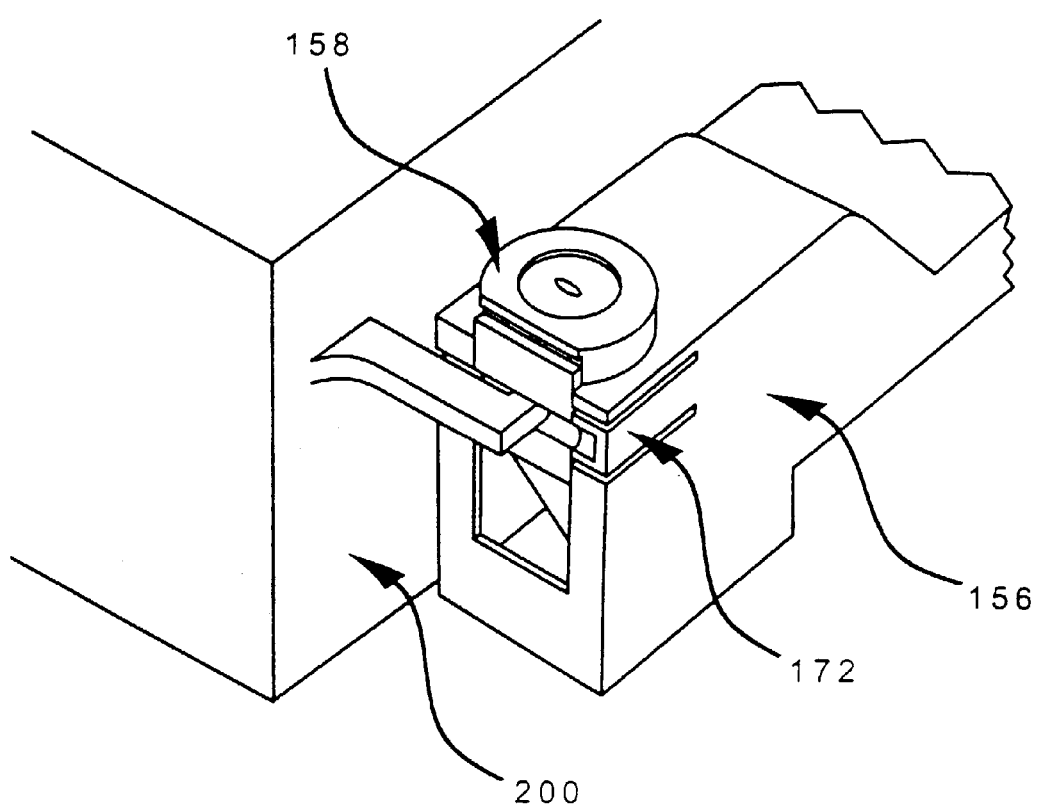
FIG. 15 shows a perspective view of interaction between a drug cassette and a mating surface when the two are partially engaged.
Figure 16:
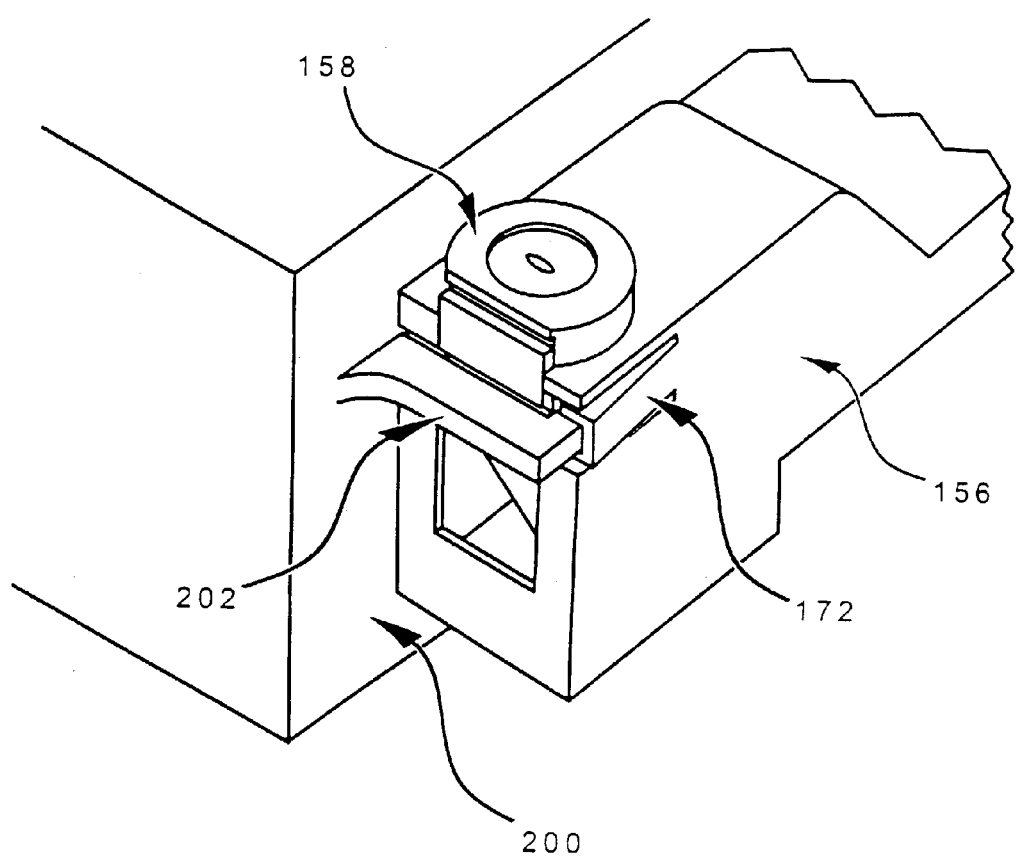
FIG. 16 shows a perspective view of interaction between a drug cassette and a mating surface when the two are engaged and mated.

The vial holder is presented to the spike assembly with an inverted vial to be spiked when the vial holder moves down against the spike sheath 158. If there is no vial in the vial holder, downwards travel of the vial holder may then expose the spike, posing a risk of a sharps injury. Particular embodiments of the invention check for the presence of a vial before initiating downwards travel of the vial holder. Checking for the presence of a vial may be implemented with sensors, including Quality Assurance Modules (QAM) such as those described in U.S. patent application No. 10/252,818 filed Sep. 24, 2002 and/or software or via mechanical means. The invention may also check if the vial is valid, e.g., of known origin and quality control and not past its expired date. When the vial holder moves down, spike 163 is unsheathed through opening 188 and pierces the vial stopper thereby placing lumens 14a and 14b inside the inverted vial. The vial holder may engage the lip 191 and step 180 of spike sheath 158 such that when the vial holder moves up to unlike a vial, the vial holder drags spike sheath 158 upwards and re-sheaths spike 163. A cut-out 194 in spike sheath 158 may be included to provide clearance for mounting flange 170 when spike sheath 158 travels downwards. A groove 192 on portion 190 may be provided with groove 192 of movable member 172 so as to accept edge 204 of peg 202 that is provided with mating surface 200 (FIG. 14). Edges 189 on both sides of portion 190 prevent spike sheath 158 from rotating within cavity 176 such that spike sheath 158 is only free to move in a vertical axis. Edges 189 also act as guides for vertical travel of spike sheath 158. FIG. 13a shows how spike sheath 158 deploys upwards to sheath spike 163 while protuberance 182 engages with lever arm 166 to close stopcock 168 thus preventing flow in drug lumen 14b of spike 163. FIG. 13b shows how spike sheath 158 retracts downwards to expose spike 163 while protuberance 186 engages with lever arm 166 to open stopcock 168 thus allowing flow in drug lumen 14b of spike 163. FIG. 14 shows part of drug cassette body 156 oriented for engagement with mating surface 200 but not yet contacting the surface. Peg 202 includes edge 204 that slides along groove 192 on drug cassette body 156 and on portion 190 of spike sheath 158. Peg 202 may also include a protuberance 206 that abuts against end 174 to deploy movable member 172 when drug cassette 150 is fully engaged with mating surface 200. Protuberance 206 travels along groove 192. A cutout behind protuberance 206 on peg 202 may be included to allow spike sheath 158 to travel downwards without catching on peg 202. FIG. 15 shows part of drug cassette body 156 partially engaged with mating surface 200. Rounded edge 204 of protuberance 206 of peg 202 is shown engaged in groove 192 on portion 190. Spike sheath 158 is still prevented by movable member 172 from moving downwards and exposing spike 163. The vial holder (not shown) is engaging step 180 and lip 191 of the spike sheath. FIG. 16 shows drug cassette body 156 substantially engaged with mating surface 200 so as to deploy movable member 172. Protuberance 206 of peg 202 is shown engaged in end 174 of groove 192 on drug cassette body 156. Movable member 172 is deployed allowing spike sheath 158 to move downwards and expose spike 163.

It is contemplated that a drug cassette 150 may be provided as part of a kit of disposable elements for use with a vial infusion system such as that described in U.S. patent application No. 09/324,759, filed Jun. 3, 1999. The cassette may also be provided alone as a disposable or reusable component of a vial infusion system. To enhance safety and to prevent accidental injury from spike 163, it is contemplated that the drug cassette 150 of the present invention may be unpacked from a kit or other packaging or storing material with spike sheath 158 in an up or deployed position so that spike 163 is not exposed. Drug cassette 150 may be secured to mating surface 200 by an automated mechanism (not shown) or manually. A drug vial (not shown) that is loaded upside down onto a vial holder (not shown) may then be positioned in place over the spike assembly 160 and against the spike sheath 158. The vial holder is constructed so as to position the vial so that the vial stopper is aligned and centered with spike sheath 158. The vial holder may also engage with lip 191 of spike sheath 158 and drives the vial and spike sheath downwards exposing spike 163 and piercing the vial stopper. The vial holder may be positioned above spike sheath 158 and moved down by an automated means provided with the infusion system. As spike sheath 158 travels downwards, lever arm 166 is actuated such that stopcock 168 or other anti-free flow device allows flow of the liquid in the vial through drug lumen 14b. Drug cassette 158 and the peristaltic and intravenous tubing (IV) may then be purged, the IV tubing connected to an IV catheter, and an infusion process to a patient begun in a manner such as that described in U.S. patent application No. 10/285,689 filed Jul. 31, 2002 and incorporated herein by reference.

At the end of an infusion case, drug infusion is stopped. The vial holder is pulled up and as it moves up it pulls the vial up and drags spike sheath 158 along with its lip 191. The upwards travel of spike sheath 158 triggers lever arm 168 closing off drug lumen 14b. As the vial is unspiked, then, spike 163 is resheathed. Once the vial is removed, drug cassette 158 can be disengaged from mating surface 200. Because drug lumen 14b is closed, none of the residual drug left in drug cassette 158 and IV tubing can free flow to a patient still connected to the IV tubing. The IV tubing may then be disconnected from the IV catheter. The intravenous tubing and drug cassette 150 with the spike assembly 160 may then be discarded in a contaminated wastebasket.

If more than one vial is required for a given case, a first vial may be unspiked as described above while leaving drug cassette 150 secured to mating surface 200. Closed drug lumen 14b prevents aspiration of air into the peristaltic and IV tubing such that there is no need to purge or prime the IV and/or peristaltic tubing again after changing vials. A new vial may then be loaded in the vial holder and spiked as described above. The vials can be changed in this manner as many times as needed until a case is concluded.

The invention claimed is:

1. A cassette for use with an intravenous infusion apparatus including a pumping mechanism which administers an infusate to a patient, wherein said cassette is removably attachable to the intravenous infusion apparatus, and wherein said cassette comprises:
   a drug container entry mechanism having an infusate flow umen configured such that infusate flows from the container and into the flow lumen;
   a sheath for said entry mechanism, wherein said sheath is configured so that said drug container entry mechanism is not unsheathed until said cassette is safely engaged with a mating surface of said intravenous infusion apparatus;
   a means for securing an infusate delivery conduit to the infusate flow lumen such that infusate can flow from the flow lumen into the delivery conduit;
   a means for preventing flow of infusate from the flow lumen into the delivery conduit and into a patient in an uncontrolled manner; and
   an indexing means for aligning the cassette when the cassette is attached to the intravenous infusion apparatus in a manner that allows proper administration of infusate to the patient.

2. The cassette of claim 1, wherein said drug container entry mechanism is a trocar assembly having a spike with a sharp tip configured for promoting puncturing and cutting of a membrane while minimizing lateral movement of said membrane's fibers, said sharp tip including at least two cutting surfaces.

3. The cassette of claim 2, wherein said spike includes a cross-section and at least two bevels across portions of said cross-section such that the area of the cross section increases with increasing distance from the tip of said spike along the longitudinal centerline, the rate of change of the cross sectional area being minimized.

4. The cassette of claim 2, wherein said spike includes two lumens with the openings of said lumens located at or near said sharp tip.

5. The cassette of claim 4, wherein said spike is manufactured of plastic by injection molding.

6. The cassette of claim 4, wherein said spike has a cross-sectional shape that looks like a rectangle with equal semi-circles replacing two opposite sites of the rectangle and curved outward from the center of said rectangle.

7. The cassette of claim 6, wherein said cross-sectional shape includes three beveled surfaces.

8. The cassette of claim 6, wherein said spike includes a bevel across the entire cross-section at an angle between 70 degrees and 80 degrees from a plane extending perpendicular to the longitudinal centerline of said spike.

9. The cassette of claim 8, wherein the width of said cross-sectional shape is between 0.14 inches to 0.16 inches at the widest point.

10. The cassette of claim 8, wherein the thickness of said cross-sectional shape is between 0.06 inches to 0.08 inches.

11. The cassette of claim 6, wherein said spike includes two bevels extending down from a line spanning the cross-sectional thickness of said spike.

12. The cassette of claim 4, wherein said spike has a cross-sectional shape like a diamond.

13. The cassette of claim 12, wherein said diamond shaped cross-section includes three beveled surfaces.

14. The cassette of claim 4, wherein said spike has a cross-sectional shape that looks like a trapezoid with semi-circles of different diameters replacing two opposite sides of the trapezoid and curved outward from the center of said trapezoid.

15. The cassette of claim 4, wherein said spike has a cross-sectional shape like a stretched hexagon.

16. The cassette of claim 4, wherein said spike has a cross-sectional shape similar to that of a football.

17. The cassette of claim 4, wherein said spike has a semi-ogival cross-section.

18. The cassette of claim 1, wherein said sheath is operatively connected to said cassette and is configured for automatically covering said drug container entry mechanism upon detachment from said mating surface of said intravenous infusion apparatus.

19. The cassette of claim 1, wherein said intravenous infusion apparatus is a sedation and analgesia system.

20. A cassette for use with an intravenous infusion apparatus including a pumping mechanism which administers an infusate to a patient, wherein said cassette is removably attachable to the intravenous infusion apparatus, and wherein said cassette comprises:
   a vial spike assembly comprising a spike for entering a drug container, at least one infusate flow lumen configured such that infusate flows from the container and into the flow lumen, an outlet connector to secure an infusate delivery conduit to the infusate flow lumen such that infusate can flow from the flow lumen into the delivery conduit, and a lever arm connected to a flow control valve to prevent flow of infusate through said infusate delivery conduit in an uncontrolled manner;
   a sheath for said vial spike assembly having an interior surface and an exterior surface, wherein said sheath is configured so that said drug container entry mechanism remains sheathed until said cassette is safely engaged with a mating surface of said intravenous infusion apparatus; and
   an indexing means for aligning the cassette when the cassette is attached to the intravenous infusion apparatus in a manner that allows proper administration of infusate to the patient.

21. The cassette of claim 20, wherein said sheath comprises one or more protuberances located on said interior surface to engage with said lever arm of said vial spike assembly to close and open said flow control means as said sheath moves to respectively cover and uncover said vial spike assembly.

22. The cassette of claim 21, wherein said sheath further comprises on said exterior surface mechanical means to engage a holder for said drug container and mechanical means to engage said sheath with said intravenous infusion apparatus.

23. The cassette of claim 20, wherein said vial spike assembly further comprises an air filter housing to house a filter element that filters out airborne disease organisms from the ambient air.

24. The cassette of claim 23, wherein said air filter housing includes an integrated air filter media holder.

25. A method for extracting from a vial infusate for use in an intravenous infusion apparatus comprising the steps of:
   providing a cassette with a vial trocar assembly, said trocar assembly having a spike with an infusion flow lumen and a means to prevent infusate flow from said lumen, and a sheath, wherein said sheath is configured so that said spike is not unsheathed until said cassette is safely engaged with a matins surface of said intravenous infusion apparatus;

affixing said cassette to a drug pumping apparatus;

attaching a vial of infusate to said cassette such that said spike is simultaneously unsheathed and inserted into said vial and such that flow of infusate from said vial through said flow lumen and said delivery conduit is permitted;

initiating means to generate flow of infusate from said vial, through said flow lumen, into said delivery conduit; and upon completion of infusate delivery, removing said vial such that said spike is simultaneously removed from said vial and sheathed and such that flow of infusate from said vial through said flow lumen and said delivery conduit is simultaneously disabled.

26. The method of claim 25, comprising the additional step of purging said infusion flow lumen and said infusion delivery conduit immediately following said step of attaching a vial.

27. The method of claim 25, comprising the additional step of securing said infusion delivery conduit against said intravenous infusion apparatus.

28. The method of claim 25, comprising the additional step of attaching a second vial of infusate.

* * * * *